United States Patent
Bakos et al.

(10) Patent No.: US 10,631,865 B2
(45) Date of Patent: Apr. 28, 2020

(54) TISSUE COMPRESSION DEVICE WITH FEATURES TO CONTAIN NEEDLES AND SUTURE DURING PACKAGING AND PLACEMENT IN BODY

(71) Applicant: ETHICON LLC, Guaynabo, PR (US)

(72) Inventors: Gregory J. Bakos, Mason, OH (US); John V. Hunt, Cincinnati, OH (US); Daniel W. Price, Loveland, OH (US); Nicholas B. Van Stolk, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 448 days.

(21) Appl. No.: 15/419,151

(22) Filed: Jan. 30, 2017

(65) Prior Publication Data
US 2018/0214152 A1   Aug. 2, 2018

(51) Int. Cl.
*A61B 17/11*  (2006.01)
*A61B 17/04*  (2006.01)
*A61B 17/06*  (2006.01)
*A61B 17/00*  (2006.01)

(52) U.S. Cl.
CPC ...... *A61B 17/1114* (2013.01); *A61B 17/0401* (2013.01); *A61B 17/06* (2013.01); *A61B 17/11* (2013.01); *A61B 2017/00876* (2013.01); *A61B 2017/06057* (2013.01); *A61B 2017/1139* (2013.01)

(58) Field of Classification Search
CPC . A61B 17/1114; A61B 17/0401; A61B 17/06; A61B 2017/1103; A61B 2017/1107; A61B 2017/1139; A61B 2017/1142; A61B 2017/06057; A61B 2017/00876

USPC ........................................................ 206/63.3
See application file for complete search history.

(56) References Cited

U.S. PATENT DOCUMENTS

| 5,733,293 A | * | 3/1998 | Scirica | ............. | A61B 17/06133 |
| | | | | | 206/339 |
| 7,041,110 B2 | | 5/2006 | Yencho et al. | | |
| 8,968,339 B2 | * | 3/2015 | Malkowski | ........ | A61B 17/0625 |
| | | | | | 606/144 |

(Continued)

FOREIGN PATENT DOCUMENTS

WO   WO 2014/055193 A1   4/2014

OTHER PUBLICATIONS

U.S. Appl. No. 15/298,816, filed Oct. 20, 2016.

(Continued)

*Primary Examiner* — Diane D Yabut
(74) *Attorney, Agent, or Firm* — Frost Brown Todd LLC

(57) ABSTRACT

An exemplary tissue compression device for forming an anastomosis includes a first device portion having a first mating surface, a first base wall recessed from the first mating surface so as to define a first inner recess, and a first set of suture bores extending through the first base wall and opening to an outer periphery of the first device portion. A second device portion of the device has a second mating surface, a second base wall recessed from the second mating surface so as to define a second inner recess, and a second set of suture bores extending through the second base wall and opening to an outer periphery of the second device portion. The first and second device portions are configured to compress tissue positioned between the first and second mating surfaces.

20 Claims, 17 Drawing Sheets

(56) References Cited

U.S. PATENT DOCUMENTS

| | | |
|---|---|---|
| 9,364,238 B2 | 6/2016 | Bakos et al. |
| 2003/0074023 A1* | 4/2003 | Kaplan ............ A61B 17/00234 606/228 |
| 2005/0101976 A1* | 5/2005 | Kato ..................... A61B 17/11 606/153 |

OTHER PUBLICATIONS

U.S. Appl. No. 15/419,086, filed Jan. 30, 2017.
U.S. Appl. No. 15/419,102, filed Jan. 30, 2017.
U.S. Appl. No. 15/419,132, filed Jan. 30, 2017.
U.S. Appl. No. 61/697,845, filed Sep. 7, 2012.
International Search Report and Written Opinion dated Apr. 26, 2018 for Application No. PCT/IB2018/050357, 12 pgs.

\* cited by examiner

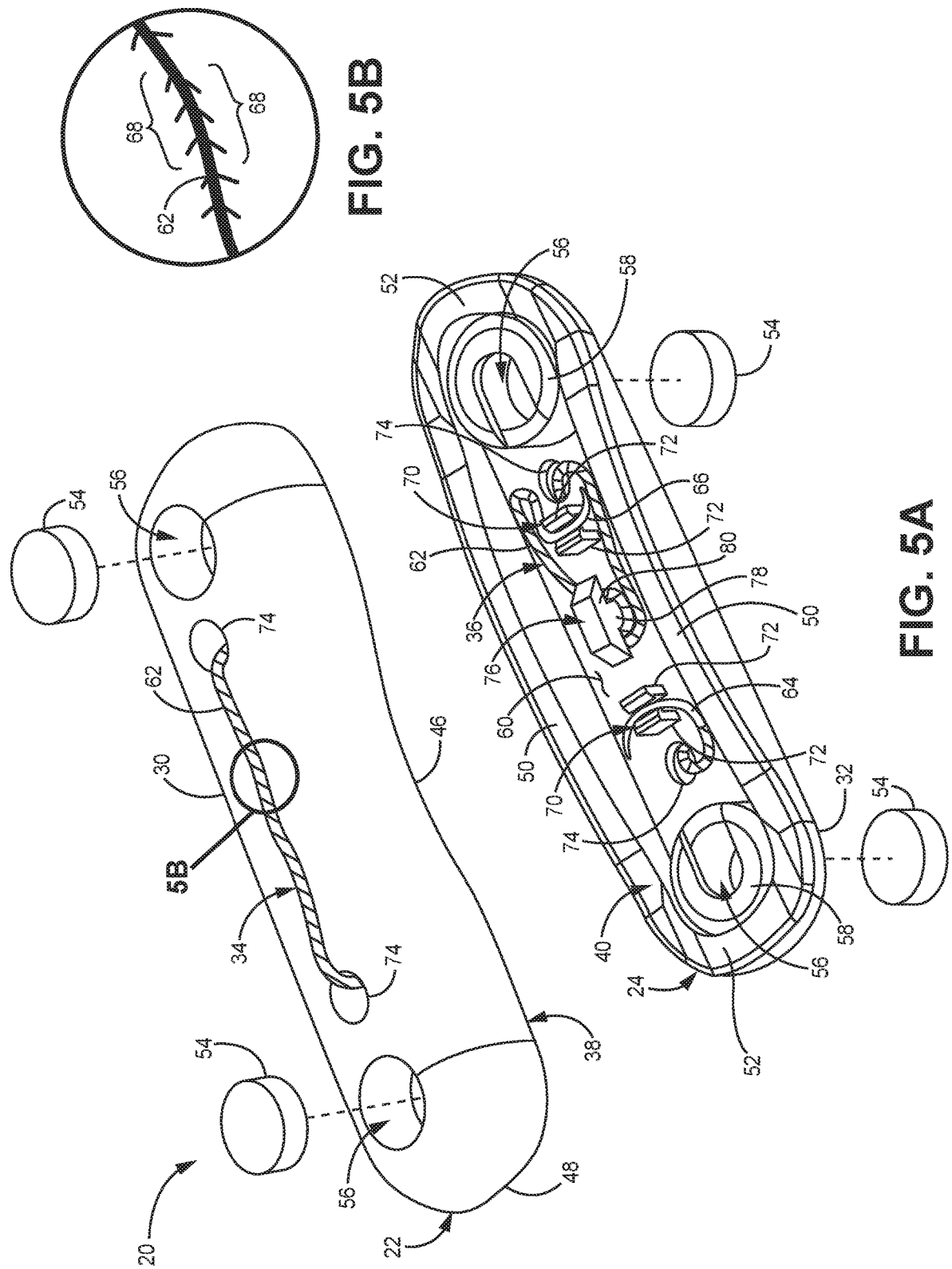

TISSUE COMPRESSION DEVICE WITH FEATURES TO CONTAIN NEEDLES AND SUTURE DURING PACKAGING AND PLACEMENT IN BODY

BACKGROUND

In some instances, it may be desirable to provide a side-to-side anastomosis between two naturally occurring lumens within a patient's body. By way of example only, it may be desirable to provide an anastomosis between two portions of a patient's gastrointestinal tract, such as between the patient's duodenum and the patient's ileum. In some patients, it may improve glucose control, serve as a treatment for type 2 diabetes, and/or provide other results when the jejunum is diverted by an anastomosis. In such a procedure, a first enterotomy may be formed in the sidewall of the duodenum while a second enterotomy is formed in the sidewall of the ileum. The sidewalls may then be positioned adjacent to each other to form an anastomosis between the portions of the duodenum and the ileum in which the enterotomies are formed, as described in greater detail below. The anastomosis establishes direct fluid communication between the adjacent portions of the duodenum and ileum, enabling at least some nutrient-rich chyme to pass through the anastomosis to travel from the duodenum directly to the ileum without passing through the jejunum. In other variations in which the anastomosis is positioned at other locations within the gastrointestinal tract, some chyme may pass through a shortened portion of the jejunum. In either case, the anastomosis enables accelerated passage of nutrient-rich chyme through the gastrointestinal tract.

One or more devices may be positioned within the first and second enterotomies to hold the sidewalls of the duodenum and ileum together, thereby holding the first and second openings in alignment with each other and maintaining patency through the openings. The device or devices may compress the tissue, which may ultimately result in a serosa-to-serosa adhesion that secures the duodenum sidewall to the ileum sidewall. In addition, tissue captured in the device or devices may eventually necrose, such that the device or devices is/are eventually released into the gastrointestinal tract and subsequently passed through the bowels. Traditional examples of anastomosis devices include Denan's rings and the Murphy button. Examples of anastomosis procedures and associated devices are taught in U.S. Provisional Patent App. No. 61/697,845, entitled "Magnetic Compression Anastomosis Device," filed Sep. 7, 2012, the disclosure of which is incorporated by reference herein; U.S. Pat. No. 9,364,238, entitled "Method and Apparatus for Joining Hollow Organ Sections in Anastomosis," issued Jun. 14, 2016, the disclosure of which is incorporated by reference herein; and U.S. patent application Ser. No. 15/298, 816, entitled "Method for Partial Diversion of the Intestinal Tract," filed Oct. 20, 2016, the disclosure of which is incorporated by reference herein.

While a variety of anastomosis devices and methods have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements, and in which:

FIG. 5A depicts a disassembled perspective view of the tissue compression device of FIG. 3, showing first and second device halves thereof equipped with first and second suture devices, respectively;

FIG. 5B depicts an enlarged view of a portion of a first barbed suture shown in FIG. 5A;

Figure 1:
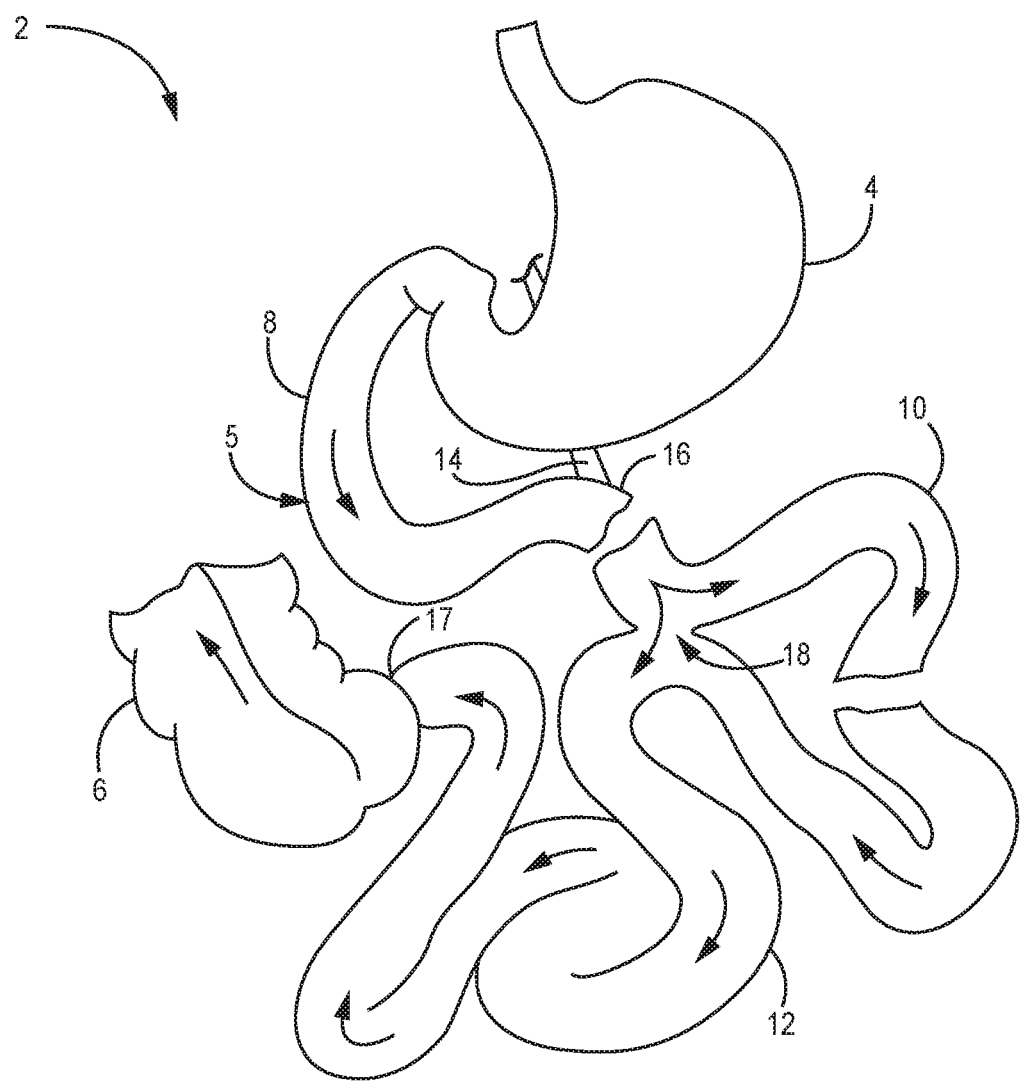
FIG. 1 depicts a diagrammatic view of a portion of a patient's digestive system, showing an exemplary side-by-side anastomosis formed in the small intestine.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Intestinal Anastomosis

As noted above, it may be desirable to provide an anastomosis between two anatomical structures within a patient's body, such as two portions of a patient's gastrointestinal tract. FIG. 1 shows an exemplary portion of a gastrointestinal tract (2) including, in downstream order, a stomach (4), a small intestine (5), and a large intestine (6). The small intestine (5) is subdivided into three portions: the duodenum (8), the jejunum (10), and the ileum (12), listed in downstream order. The duodenum (8) is supported by a suspensory muscle (14) known as the ligament of Treitz, and transitions into the jejunum (10) at the duodenojejunal flexure (16). The ileum (12) transitions into the large intestine (6) at the ileocecal junction (17), also known as the ileocecal valve.

Figure 2:
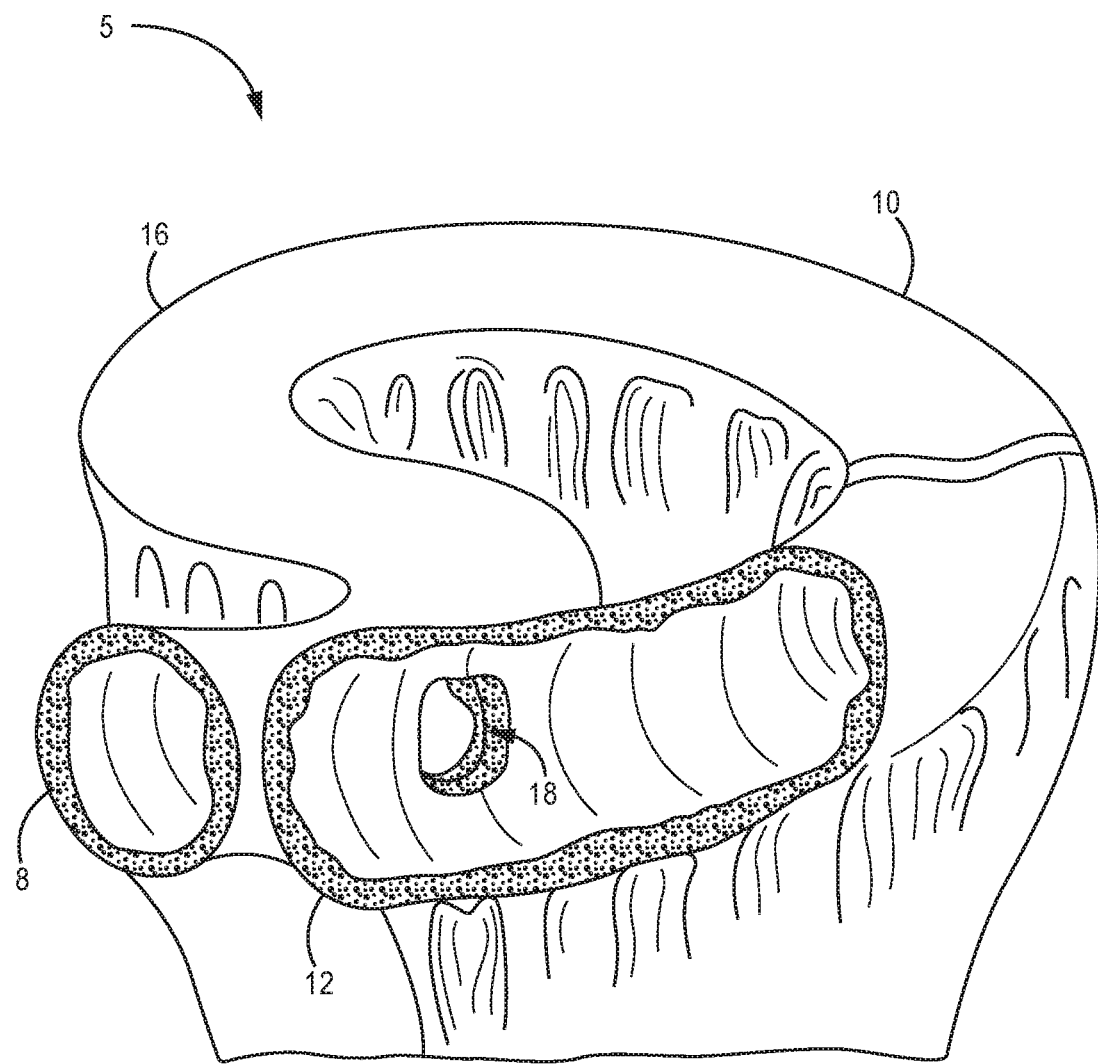
FIG. 2 depicts a partial perspective view of another exemplary side-by-side anastomosis formed in the small intestine.

The gastrointestinal tract (2) is shown including an exemplary anastomosis (18) formed between a proximal portion of the jejunum (10) and the ileum (12). The anastomosis (18) has an inlet side formed through a sidewall of the jejunum (10) at a location adjacent to and downstream of the duodenojejunal flexure (16) and the ligament of Treitz (14). The anastomosis (18) additionally has an outlet side formed through a sidewall of the ileum (12). It will be appreciated that the anastomosis (18) may be positioned at various other suitable locations along the gastrointestinal tract (2). For example, as shown in FIG. 2, the anastomosis (18) may be formed between the duodenum (8) and the ileum (12). Additional exemplary locations of the anastomosis (18) are described in U.S. patent application Ser. No. 15/298,816, incorporated by reference above. It will be further appreciated that the anastomosis (18) may be located elsewhere within a patient's body, other than within the gastrointestinal tract (2). In that regard, it will be understood that the exemplary tissue compression devices shown and described herein may be employed to create anastomoses in various other bodily organs having an internal lumen, and thus are not limited to use in a patient's gastrointestinal tract (2).

Still referring to FIG. 1, the exemplary anastomosis (18) shown provides a pathway for direct fluid communication between the proximal portion of the patient's jejunum (10) and the ileum (12), thereby bypassing a majority of the jejunum (10) located downstream. Consequently, chyme exiting the stomach (4) may flow directly through the duodenum (8), then through the proximal portion of the jejunum (10) and directly into the ileum (12), via the anastomosis (18), without passing through the downstream portion of the jejunum (10). In some instances, a first portion of the chyme exiting the stomach (4) may flow directly from the proximal portion of the jejunum (10) to the ileum (12), via the anastomosis (18). Simultaneously, a second portion of the chyme may pass the anastomosis (18) and flow through the downstream portion of the jejunum (10), rejoining with the first portion of chyme in the ileum (12) before passing into the large intestine (6). Accordingly, the anastomosis (18) may provide a complete diversion or a partial diversion of chyme passing through the jejunum (10).

Forming a side-by-side anastomosis (18) between two portions of the gastrointestinal tract (2), positioned adjacent to one another, may be achieved using a compression device having first and second device portions that clamp intestinal tissue therebetween, as described above. In some procedures, the device portions may be introduced into the intestinal lumen via two or more enterotomies formed in the intestinal sidewalls at respective upstream and downstream locations. In other procedures, the device portions may be introduced into the intestinal lumen endoscopically, using two or more endoscopes inserted through naturally occurring body orifices and directed into the intestinal lumen from opposing directions. The exemplary tissue compression devices disclosed herein may be positioned within a patient using either of these methods, for example.

II. Exemplary Anastomosis Tissue Compression Devices

As will be described in greater detail below, the first and second device portions of the tissue compression devices disclosed herein include magnetic members that draw the device portions together magnetically. The device portions, when drawn together, compress tissue positioned therebetween with a clamping force sufficient to cause ischemia and eventual necrosis of the tissue. Once necrosis occurs, the device falls away to reveal an anastomosis, and the device is then passed downstream through the gastrointestinal tract (2).

During the procedure of installing tissue compression device portions within the intestinal tract, it may be desirable to use sutures to temporarily secure the positions of the device portions within the intestinal tract. Even if magnets are ultimately used to maintain the positions of the device portions during formation of the anastomosis, sutures may be used to secure the positions of the device portions within the intestinal tract before the device portions are brought within sufficient range of each other for their magnets to attract the device portions toward each other. Such sutures may also be used to close the enterotomies through which the device portions were inserted. Moreover, such sutures may be used to assist in drawing the device portions toward each other, to thereby bring the device portions within sufficient range of each other for their magnets to attract the compression devices further toward each other. The following description provides examples in which sutures may be integrated into portions of a tissue compression device in order to provide at least some of the above-noted enhanced functionality. Other variations will be apparent to those of ordinary skill in the art in view of the teachings herein.

Figure 3:
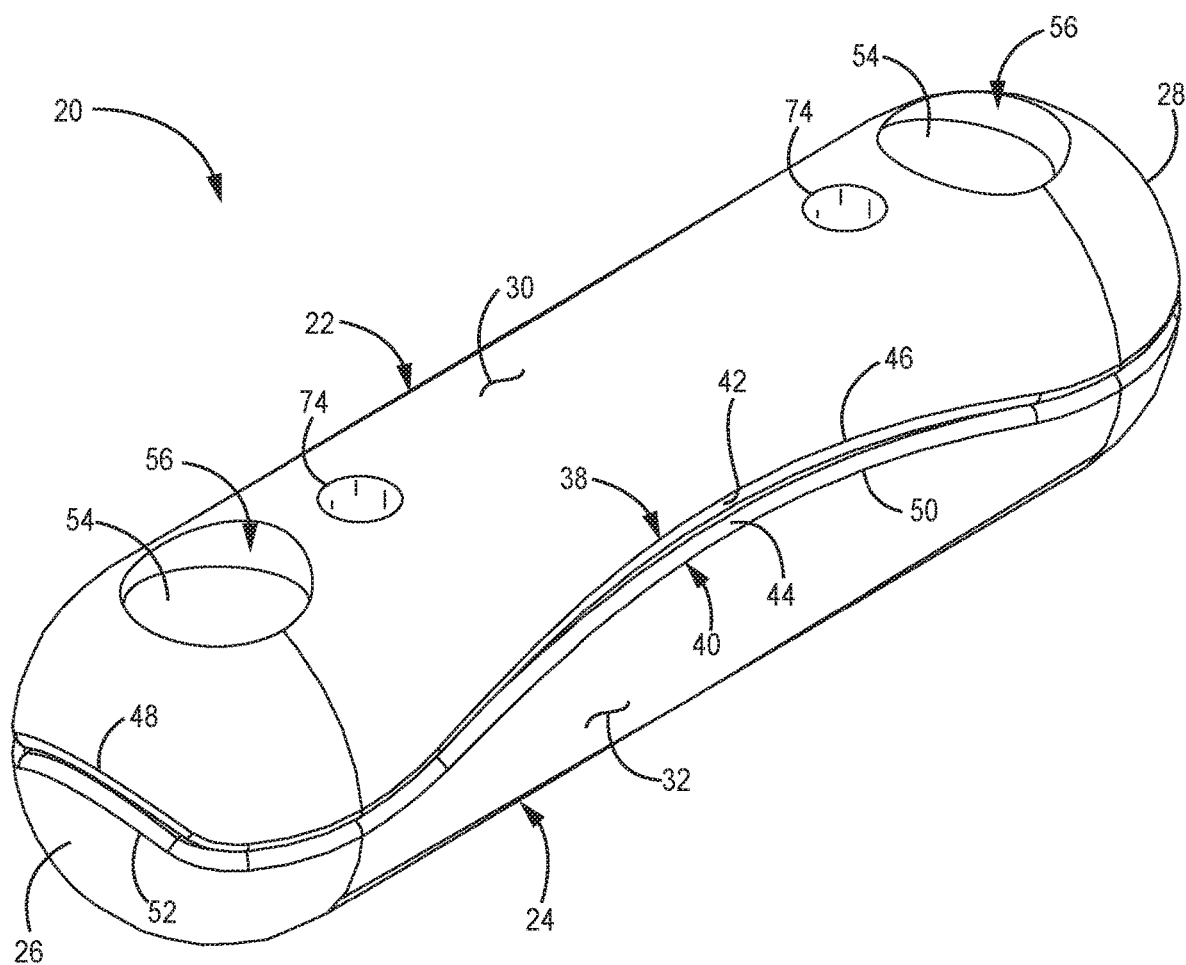
FIG. 3 depicts a perspective view of an exemplary tissue compression device for forming an anastomosis.

A. Exemplary Tissue Compression Devices Having Suture Needle Retaining Structures FIGS. 3-4B show an exemplary tissue compression device (20) for forming an anastomosis, such as a side-by-side anastomosis. The tissue compression device (20), shown in an assembled configuration, includes a first device half (22) and a second device half (24) that mate together to define an elongate device body that extends along a longitudinal device axis between a convexly rounded first end (26) and a convexly rounded second end (28). The first device half (22) includes a first rigid body having a first rounded outer periphery (30), and the second device half (24) includes a second rigid body having a second rounded outer periphery (32). The body of each device half (22, 24) of the present example is formed as a unitary structure having a length, measured along the device axis, that is greater than its width, measured transverse to the device axis. Accordingly, when the device halves (22, 24) mate together, as shown in FIG. 3, they define a device body having a fully rounded outer periphery and a length that is greater than its width so as to define an elongate, low-profile, pill-shaped structure.

Figure 4A:
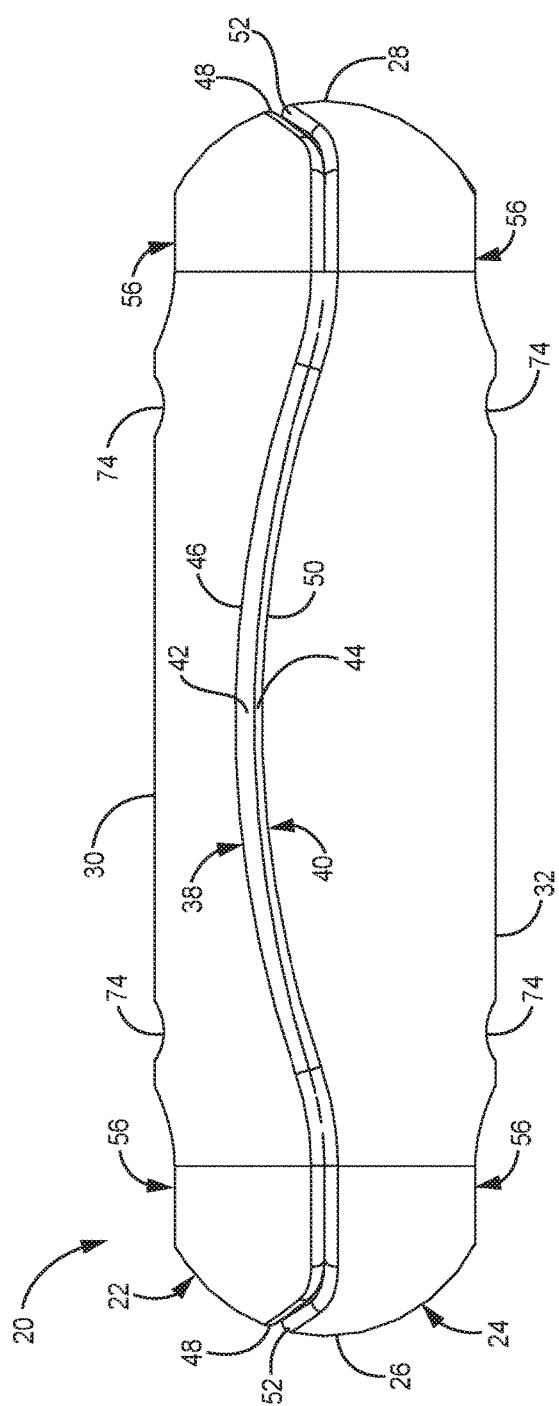
FIG. 4A depicts a side elevational view of the tissue compression device of FIG. 3.
Figure 4B:
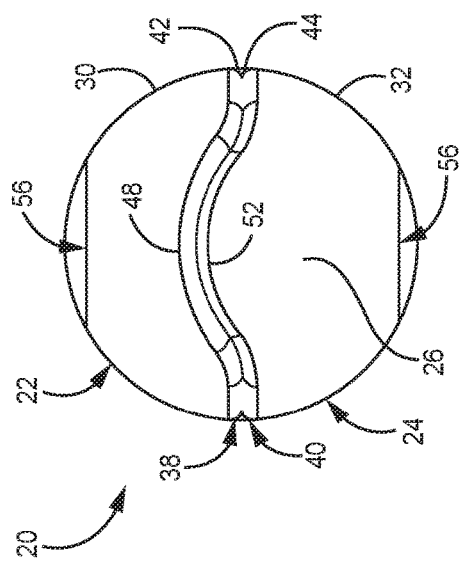
FIG. 4B depicts an end elevational view of the tissue compression device of FIG. 3.

As best shown in FIGS. 4A and 4B, the tissue compression device (20) is formed with a transverse cross-section having a rounded shape to provide the device (20) with a rounded and smooth outer periphery that is atraumatic to patient tissue. As best shown in FIG. 4B, the exemplary device (20) is formed with a generally circular shaped cross-section. Additionally, as shown in FIG. 4A, the circular cross-section is uniform in diameter along a medial portion of the device (20) extending between its first and second rounded ends (26, 28). In alternative variations, the device (20) may be formed with a transverse cross-section of various other shapes, such as various rounded shapes, and the cross-section may be uniform or non-uniform (e.g., tapered) along a length of the device (20).

FIG. 5A shows the tissue compression device (20) in a disassembled configuration, and equipped with a first suture device (34) supported by the first device half (22), and a second suture device (36) supported by the second device half (24). For illustrative purposes only, the first device half (22) is shown in an upper position and the second device half (24) is shown in a lower position. In that regard, it will be appreciated that relative positional terms including "upper," "lower" and similar terms as may be used herein are illustrative only and are not limiting of the features to which they refer nor of the various orientations in which the device (20) may be employed.

As best shown in FIGS. 4A-5A, the first device half (22) includes a first mating surface (38) that extends continuously about a perimeter of the mating side of the first device half (22). Similarly, the second device half (24) includes a second mating surface (40) that extends continuously about a perimeter of the mating side of the second device half (24). Each mating surface (38, 40) includes a rounded outer edge (42, 44) that transitions smoothly to the rounded outer periphery (32, 36) of the respective device half (22, 24).

As best shown in FIGS. 4A and 4B, the first and second mating surfaces (38, 40) are shaped with complementary contours that facilitate alignment of the device halves (22, 24) with one another, and enable the device halves (22, 24) to mate together in contacting engagement along the full length of the mating surfaces (38, 40). More specifically, in the present example the first mating surface (38) includes elongate concave side portions (46) extending generally parallel to the device axis, and concave end portions (48) extending generally transverse to the device axis. The second mating surface (40) includes elongate convex side portions (50) extending generally parallel to the device axis, and convex end portions (52) extending generally transverse to the device axis. The elongate concave side portions (46) are formed with a contour that complements a contour of the elongate convex side portions (50). Similarly, the concave end portions (48) are formed with a contour that complements a contour of the convex end portions (52).

As best shown by a comparison of FIGS. 4A and 4B, the side portions (46, 50) of the first and second mating surfaces (38, 40) are formed with a first radius of curvature, and the end portions (48, 52) are formed with a second, differing radius of curvature. The mating surfaces (38, 40) may exhibit additional geometric features as disclosed in U.S. patent application Ser. No. 15/419,132, entitled "Elongated Tissue Compression Device System With Smooth Outer Contour and Orthogonal Curved Aligning Surfaces," filed on Jan. 30, 2017 published as U.S. Pub. No. 2018/0214149 on Aug. 2, 2018, the disclosure of which is hereby incorporated by reference herein. In other variations, though not shown, the mating surfaces (38, 40) may be formed with various alternative configurations of complementary contours, or with fully or partially planar configurations, for example.

Still referring to FIG. 5A, the first device half (22) houses a first pair of magnetic members (54), and the second device half (24) houses a second pair of magnetic members (54). Each magnetic member (54) is received within a respective socket (56) of a respective magnet retaining structure (58) arranged at a respective end of the corresponding device half (22, 24). Each socket (56) extends generally transversely toward the device axis, and opens at a first end to the rounded outer periphery (30, 32) of the respective device half (22, 24), and opens at a second end to the mating side of the device half (22, 24).

In the present example, each magnetic member (54) is generally disc-like or cylindrical in shape, and is fixed at an inner end of its respective socket (56), such as by bond or press fit, for example. In other variations, the magnetic members (54) may be threadedly engaged with their sockets (56), or one or more of the magnetic members (54) may be slidable within its socket (56) and provided with a latching feature. Such latching feature may be configured to lockingly engage an opposing magnetic member (54) of the other device half (22, 24), for example as disclosed in U.S. patent application Ser. No. 15/419,086, entitled "Magnetic Tissue Compression Device with Backup Mechanical Latch," filed on Jan. 30, 2017, issued as U.S. Pat. No. 10,206,682 on Feb. 19, 2019, the disclosure of which is hereby incorporated by reference herein.

In the present example, the magnetic members (54) are in the form of, or otherwise include, permanent magnets. In that regard, each magnetic member 54 is arranged within its respective device half (22, 24) so as to exhibit a magnetic polarity at the mating side of its device half (22, 24) that is opposite of the magnetic polarity exhibited by the opposing magnetic member (54) at the mating side of the other device half (22, 24). In some variations, the magnetic members (54) of each device half (22, 24) may exhibit opposite magnetic polarities at the mating side of their device half (22, 24). In other variations, both of the magnetic members (54) of the first device half (22) may exhibit a first magnetic polarity at the mating side of the first device half (22), while both of the magnetic members (54) of the second device half (24) exhibit an opposite second magnetic polarity at the mating side of the second device half (24). In such variations, the magnetic members (54) of each device half (22, 24) are configured to magnetically attract the magnetic members (54) of the other device half (22, 24). Accordingly, the device halves (22, 24) are configured to magnetically draw together and compress tissue positioned therebetween to form an anastomosis, as described in greater detail below.

While the magnetic members (54) are shown in the form of permanent magnets, in alternative variations they may be in the form of electromagnets, for example. In other variations, the magnetic members (54) may include a combination of one or more permanent magnets and one or more electromagnets. In that regard, the tissue compression device (20) may further include a circuit assembly having one or more electromagnets and/or one or more illumination devices or other suitable electrical elements, for example as generally disclosed in U.S. patent application Ser. No. 15/419,102, entitled "Battery Powered Electromagnetic Tissue Compression Device," filed on Jan. 30, 2017, published as U.S. Pub. No 2018/0214151 on Aug. 2, 2018, the disclosure of which is hereby incorporated by reference herein.

Figure 6A:
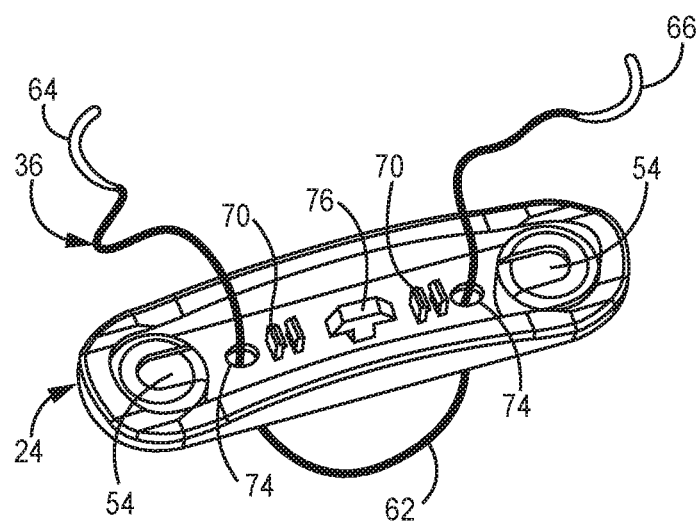
FIG. 6A depicts a perspective view of the second device half and the second suture device of FIG. 5A, showing the second suture device arranged according to an initial step of an exemplary suturing procedure.
Figure 6B:
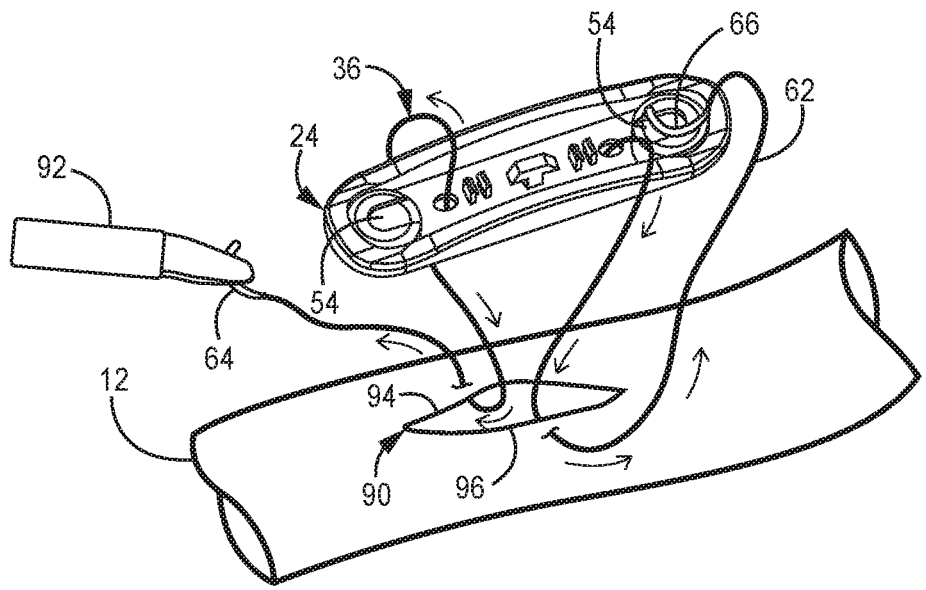
FIG. 6B depicts a perspective view of the second device half of FIG. 5A and a portion of a small intestine, showing the second suture device arranged according to a subsequent step of the exemplary suturing procedure of FIG. 6A.
Figure 6C:
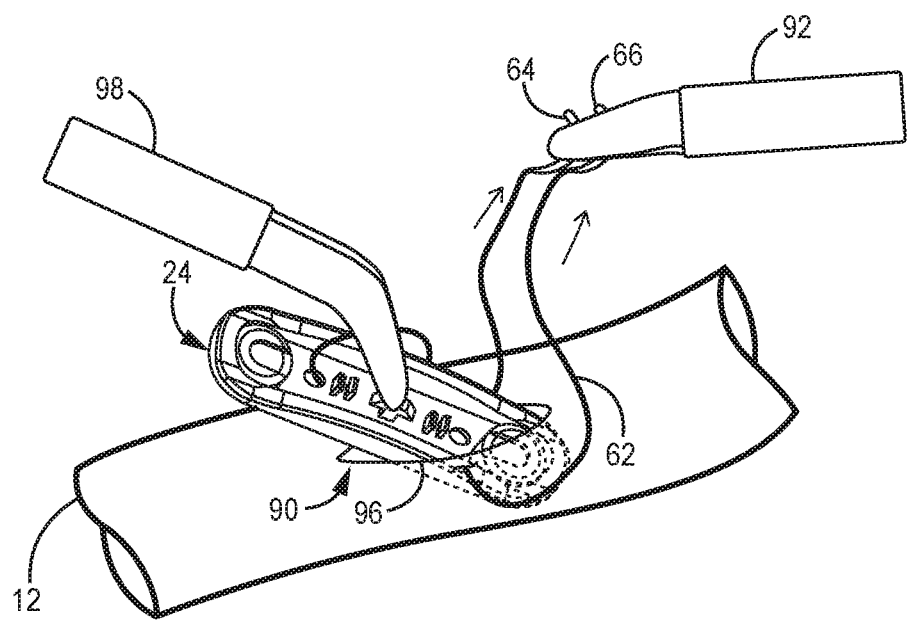
FIG. 6C depicts a perspective view of the second device half of FIG. 5A and the small intestine portion, showing the second device half being inserted through an enterotomy formed in the small intestine portion and the second suture device arranged according to a subsequent step of the exemplary suturing procedure of FIG. 6A.
Figure 6D:
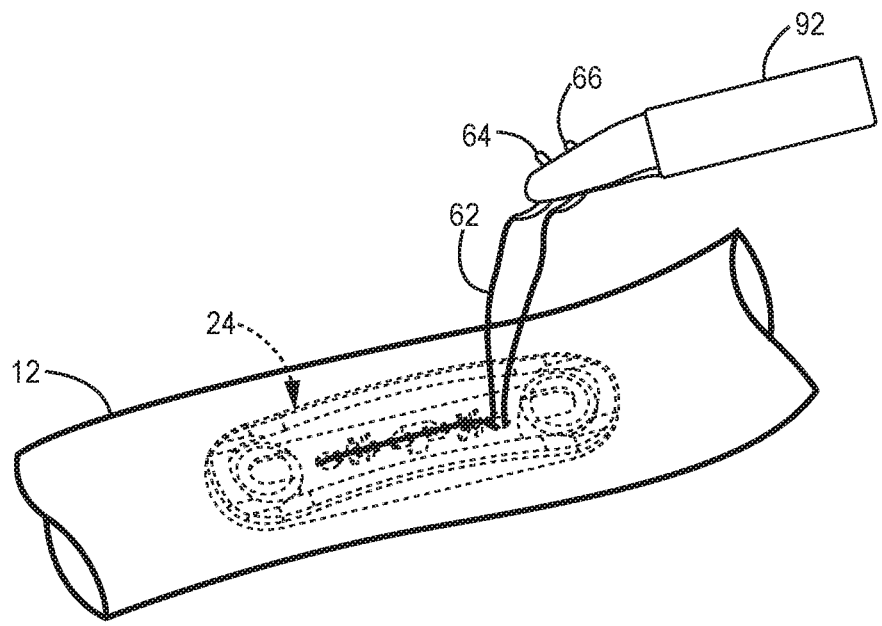
FIG. 6D depicts a perspective view showing the second device half of FIG. 5A arranged within the small intestine portion, and the second suture device arranged according to a subsequent step of the exemplary suturing procedure of FIG. 6A.
Figure 6E:
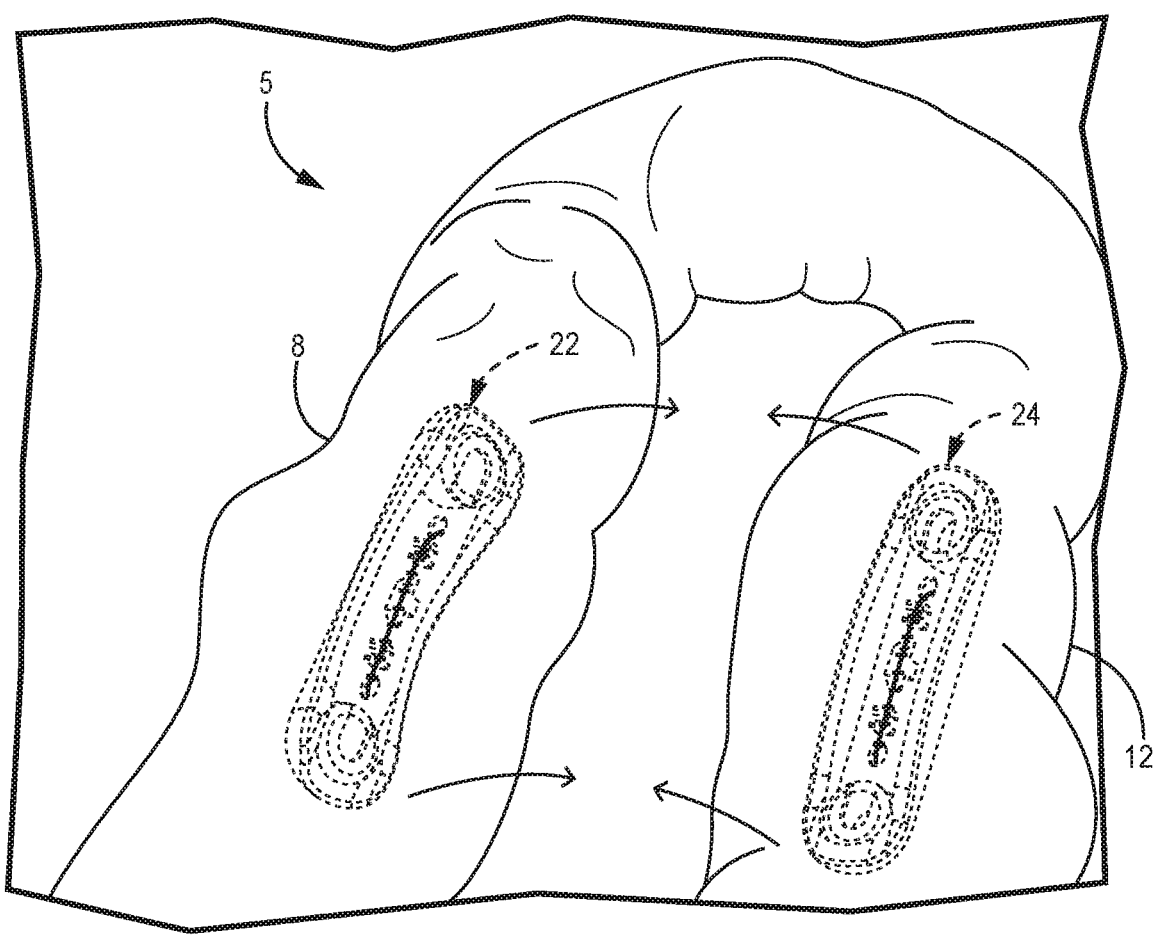
FIG. 6E depicts a perspective view of the small intestine after deployment of the first and second device halves of the tissue compression device of FIG. 5A into respective adjacent portions of the small intestine using the exemplary suturing procedure of FIG. 6A.
Figure 6F:
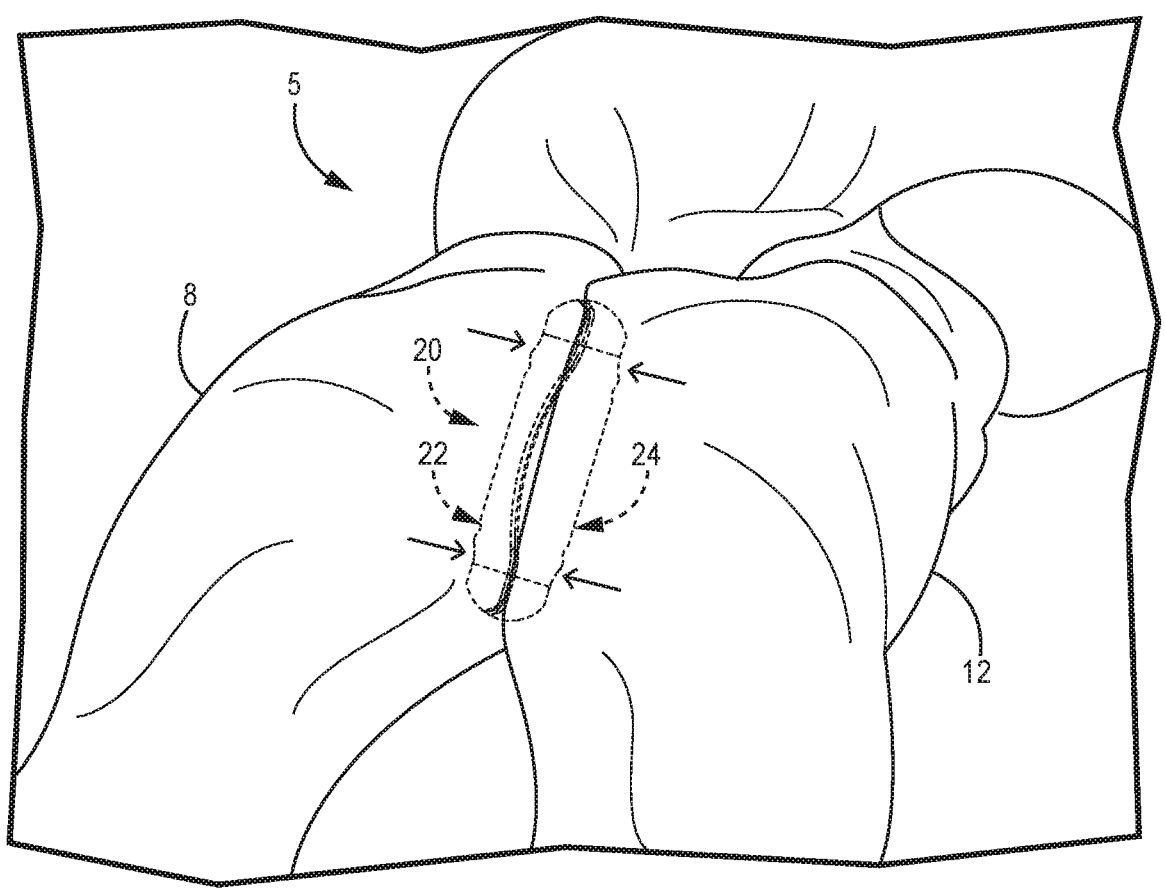
FIG. 6F depicts a perspective view of the small intestine after deployment of the first and second device halves of the tissue compression device of FIG. 5A, showing the first and second device halves arranged in confronting relation and magnetically drawing together to compress tissue therebetween for forming an anastomosis.

Each device half (22, 24) further includes a base wall (60) that is recessed inwardly relative to its respective mating surface (38, 40), and from which the magnet retaining structures (58) project toward the device axis. The recessed base wall (60) of the first device half (22) defines a first inner recess, as shown in FIG. 6H, and the recessed base wall (60) of the second device half (24) defines a second inner recess, as shown in FIGS. 5A and 6H. As shown best in FIG. 6H, when the device halves (22, 24) are combined so that their mating surfaces (38, 40) confront one another, the first and second inner recesses communicate to define a closed interior cavity bounded by the recessed base walls (60) and by the magnet retaining structures (58).

As shown in FIG. 5A, the first device half (22) is configured to support a first suture device (34) and the second device half (24) is configured to support a second suture device (36). Each suture device (34, 36) includes a suture, shown in the form of a barbed suture (62), and first and second suture needles, shown in the form of first and second curved suture needles (64, 66), coupled to opposed ends of the suture (62). In the present example, each suture needle (64, 66) comprises a ferrous material and is configured to be magnetically attracted by at least one of the magnetic members (54) of the respective device half (22, 24). In other versions, the suture needles (64, 66) may be completely non-ferrous, such that they are not magnetically attracted by the magnetic members (54).

FIG. 5B shows an enlarged view of the barbed suture (62) of the first suture device (34) carried by the first device half (22) in FIG. 5A. As shown, the barbed suture (62) includes a plurality of outwardly projecting barbs (68) that are configured to penetrate and embed within tissue, thereby securely anchoring the suture (62) to the tissue and eliminating the need for knots to be tied in the suture (62) to achieve such anchoring. By way of example only, barbed suture (62) may comprise a STRATAFIX™ suture by Ethicon, Inc. (Somerville, N.J.). Alternatively, any other suitable kind of suture may be used to provide barbed suture (62). It will be understood that in alternative versions, the sutures (62) may be in the form of non-barbed sutures. An exemplary suturing procedure using the sutures (62), in the form of barbed sutures, is described in greater detail below in connection with FIGS. 6A-6D.

As shown in FIG. 5A, each device half (22, 24) includes a pair of needle retaining structures, shown in the form of needle clip members (70). Each needle clip member (70) is configured to releasably engage and support a suture needle (64, 66) of a respective one of the suture devices (34, 36). The first device half (22) includes a first pair of needle clip members (70) coupled to and projecting from the recessed base wall (60) within the first inner recess. The second device half (24) includes a second pair of needle clip members (70) coupled to and projecting from the recessed base wall (60) within the second inner recess. As shown in FIG. 5A, each needle clip member (70) includes a pair of resilient clip arms (72) arranged in a confronting relationship and configured to releasably engage respective sides of a suture needle (64, 66) with a snap-fit engagement. In the present example, each clip member (70) is configured to orient a respective suture needle (64, 66) generally perpendicularly to a length of the respective device half (22, 24). In other examples, each clip member (70) may be configured to support a respective suture needle (64, 66) in various orientations other than perpendicularly to a length of the device half (22, 24).

The needle clip members (70) are aligned along a longitudinal centerline of each base wall (60), parallel to a length of the respective device half (22, 24), and are spaced apart such that each needle clip member (70) is located proximate to a respective one of the magnet retaining structures (58). In alternative versions, various other quantities and arrangements of needle clip members (70) may be provided. For example, each device half (22, 24) may include a single needle clip member (70) that is configured to releasably engage and support both suture needles (64, 66) of a suture device (34, 36). Additionally, in alternative versions, the needle retaining structures may be the form of, or otherwise incorporate, various other mechanical features apparent to a person of ordinary skill in the art as being suitable to releasably engage and support one or more suture needles (64, 66) within the inner recesses defined by the base walls (60) of the device halves (22, 24).

Still referring to FIG. 5A, each device half (22, 24) further includes a pair of suture bores (74) that extend through the respective base wall (60) in a direction transverse to the device axis, and open to the rounded outer periphery (30, 32) of the respective device half (22, 24). Each suture bore (74) is sized to slidably receive a suture device (34, 36) therethrough, as described in greater detail below. The suture bores (74) are aligned along a longitudinal centerline of the respective base wall (60), parallel to a length of the device half (22, 24), and are spaced apart such that each suture bore (74) is located proximate to a respective one of the magnet retaining structures (58). In the present example, each suture bore (74) is located between a respective needle clip member (70) and a magnet retaining structure (58). In alternative examples, various other quantities and arrangements of suture bores (74) may be provided.

As shown in FIG. 5A, each device half (22, 24) further includes a suture retaining structure shown in the form of a suture post (76) coupled to and projecting from the respective recessed base wall (60). Each suture post (76) includes a proximal stem (78) and a distal head (80) coupled to the stem (78). The head (80) flares laterally beyond the stem (78) so that the portion of a suture (62) wrapped around the stem (78) is prevented from sliding distally off the suture post (76). A distal tip of the head (80) may be chamfered to urge a suture (62) toward the stem (78) when being wound about the suture post (76). In the present example, the suture post (76) of each device half (22, 24) is arranged centrally between the magnet retaining structures (58) and in alignment with the needle clip members (70) and the suture bores (74) along a longitudinal centerline of the base wall (60). In alternative examples, the suture post (76) may be provided with various other known mechanical features suitable for retaining a portion of the suture (62) in engagement with the post (76), and in various other quantities and arrangements within the inner recess of the respective device half (22, 24).

Figure 6G:
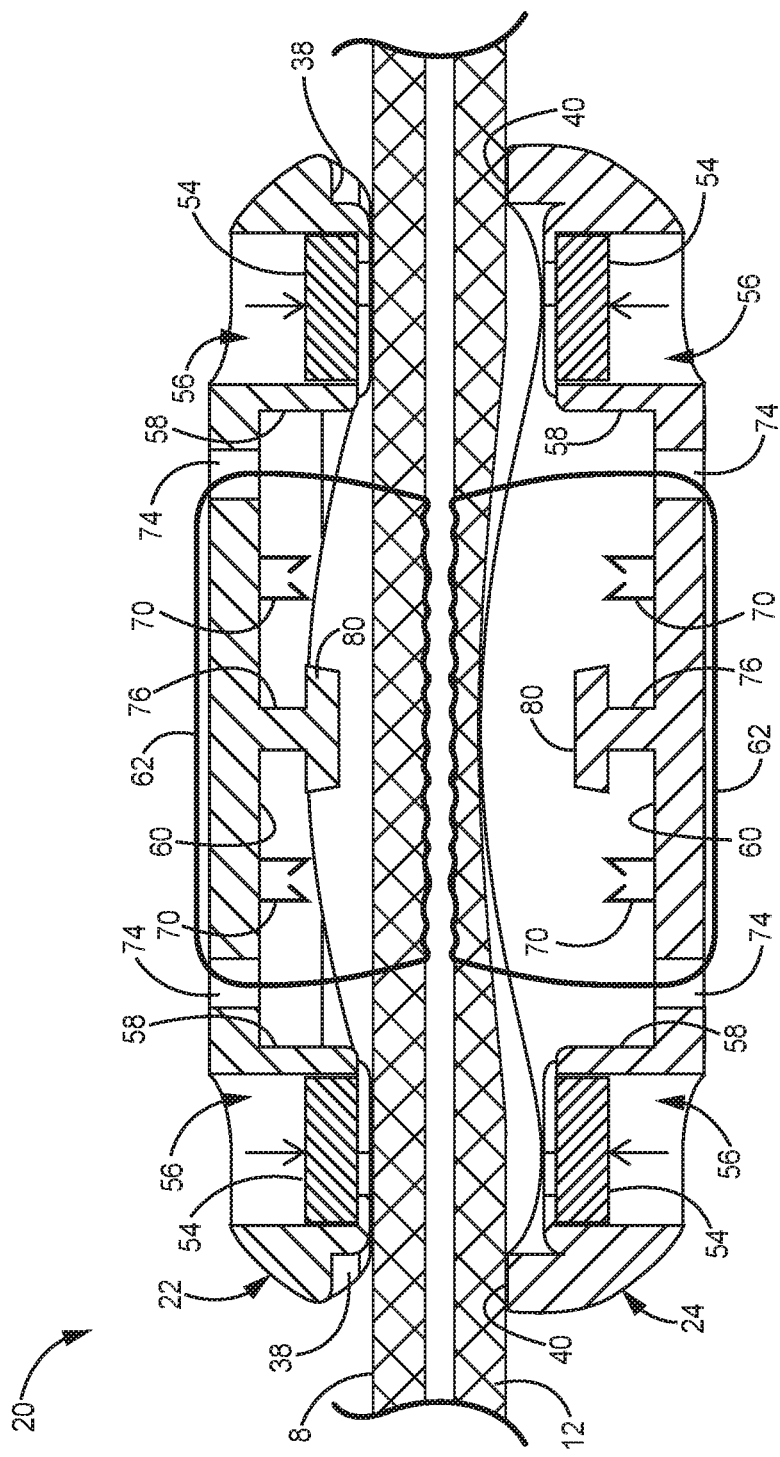
FIG. 6G depicts a side cross-sectional view of the tissue compression device of FIG. 5A positioned within the first and second portions of the small intestine of FIG. 6F, showing the first and second device halves magnetically drawing together to compress tissue therebetween.
Figure 6H:
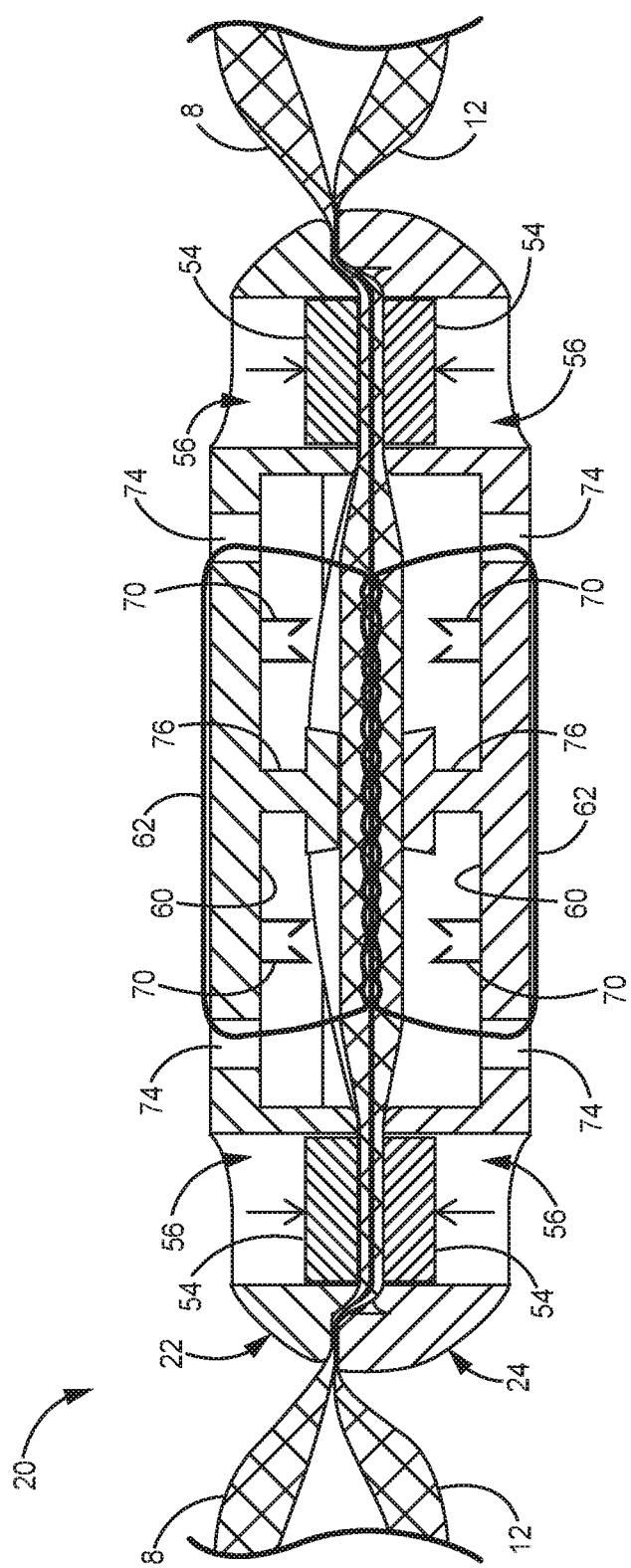
FIG. 6H depicts a side cross-sectional view of the tissue compression device of FIG. 5A positioned within the first and second portions of the small intestine of FIG. 6F, showing further compression of the tissue between the device halves and resulting necrosis of the compressed tissue.
Figure 6I:
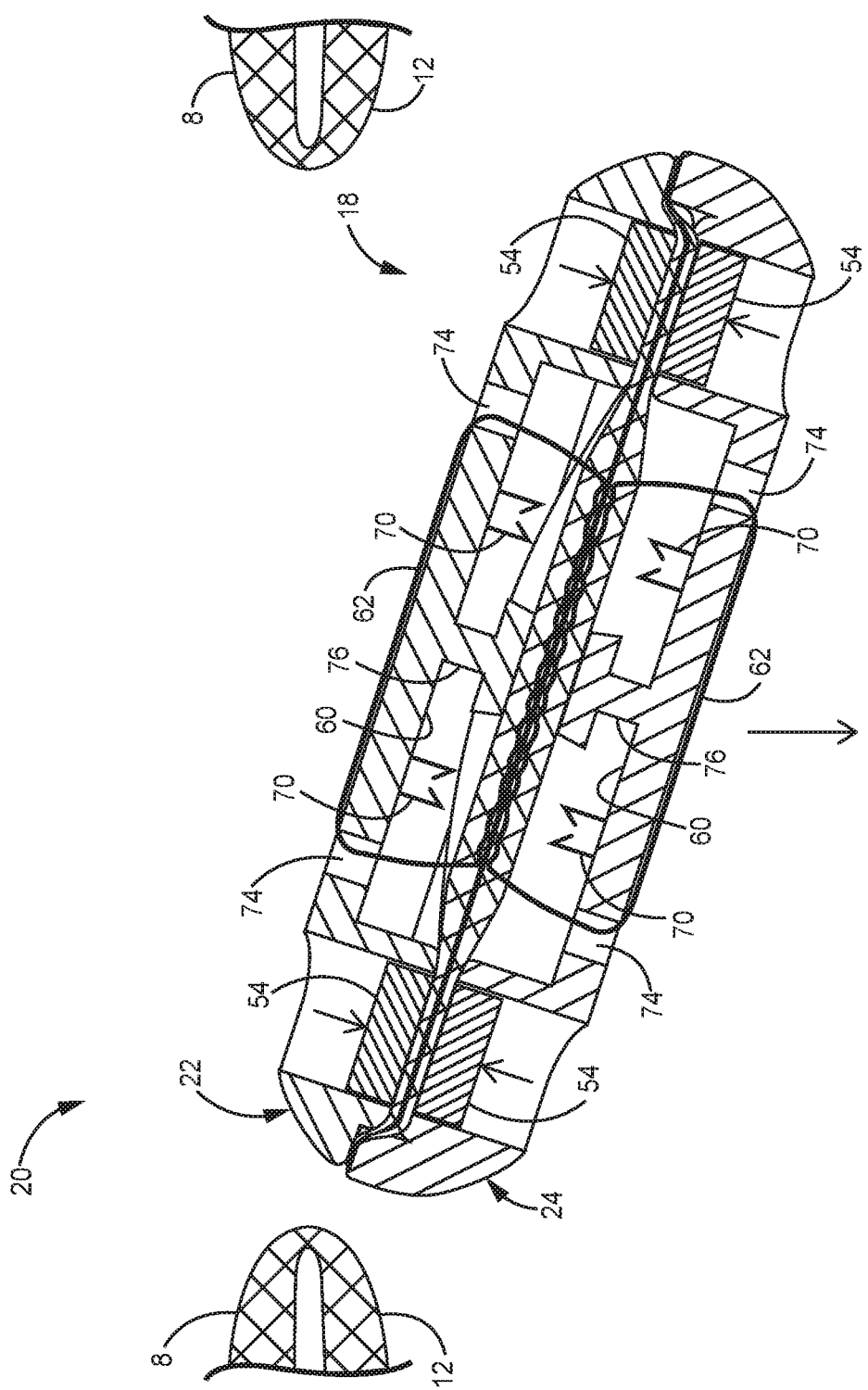
FIG. 6I depicts a side cross-sectional view of the tissue compression device of FIG. 5A arranged within the small intestine of FIG. 6F, showing the compressed tissue in a fully necrosed state and the device falling away to reveal an anastomosis between the first and second portions of the small intestine.

As shown in FIGS. 6G-6I, the needle clip members (70) and suture posts (76) of each device half (22, 24) are arranged entirely within the inner recess defined by the respective recessed base wall (60), such that distal tips of the clip members (70) and suture posts (76) do not extend beyond distal mating surfaces of the magnet retaining structures (58). Advantageously, this arrangement prevents interference of the suture posts (76) and clip members (70) of the first device half (22) with those of the second device half (24), particularly in versions in which these components align with one another when the device halves (22, 24) mate, as shown in FIG. 6G. In alternative versions, the suture post (76) and clip members (70) of the first device half (22) may be longitudinally offset from those of the second device half (24). In such alternative versions, the suture post (76) and/or one or more clip members (70) of a device half (22, 24) may project distally into the inner recess of the opposed device half (22, 24) when the device halves (22, 24) mate.

As shown in FIG. 5A, the tissue compression device (20) and the suture devices (34, 36) may be packaged together as a kit, such that the first suture device (34) is releasably retained by the first device half (22) and the second suture device (36) is releasably retained by the second device half (24). To couple a suture device (34, 36) to a respective device half (22, 24), as shown by the second device half (24) and second suture device (36) in FIG. 5A, each needle (64, 66) of the suture device (34, 36) is directed inwardly through a respective suture bore (74) of the corresponding device half (22, 24) and then snapped into the respective needle clip member (70). A slack portion of the suture (62) may then be wound around the stem (78) of the respective suture post (76), until a medial portion of the suture (62) is drawn tight across and captures a portion of the device half outer periphery (30, 32) extending between the suture bores (74). The first and second device halves (22, 24), loaded with the first and second suture devices (34, 36), may then be packaged in a compact manner and delivered to a medical professional for use. It should therefore be understood that the end user will not need to take the time to install suture devices (34, 36) in respective device halves (22, 24), as the end user will receive suture devices (34, 36) pre-installed in respective device halves (22, 24).

The tissue compression device (20) may further include various additional suitable features not shown herein, such as one or more mechanical latching mechanisms, compressible members, and/or tissue retaining clips as disclosed in U.S. patent application Ser. No. 15/419,086 filed on Jan. 30, 2017, issued as U.S. Pat. No. 10,206,682 on Feb. 19, 2019, incorporated by reference above. Other suitable features, components, and operabilities that may be incorporated into tissue compression device (20) will be apparent to those of ordinary skill in the art in view of the teachings herein.

B. Exemplary Procedure for Forming an Anastomosis Using Tissue Compression Device Having Suture Needle Retaining Structures As described above, the tissue compression device (20) may be arranged in combination with a pair of suture devices (34, 36), thereby providing a conveniently packaged kit for use by a medical professional. Having described structural features of the tissue compression device (20) and the suture devices (34, 36) above, an exemplary method of anchoring the first and second device halves (22, 24) within respective portions of a patient's gastrointestinal tract (2), and forming an anastomosis therebetween, is described below in connection with FIGS. 6A-6I. While the first and second device halves (22, 24) are shown and described as being deployed within the duodenum (8) and the ileum (12), respectively, it will be understood that the device halves (22, 24) may be deployed at various other locations within the gastrointestinal tract (2), or within other organs, at which an anastomosis is to be formed. Further, while the steps illustrated in FIGS. 6A-6D are shown in connection with anchoring the second device half (24) within the ileum (12) using the second suture device (36), it will be understood that similar steps may be employed to anchor the first device half (22) within the duodenum (8) using the first suture device (34).

FIG. 6A shows the second device half (24) in combination with the second suture device (36), after the device halves (22, 24) have been separated from one another and after the suture needles (64, 66) of the second suture device (36) have been disengaged from the needle clip members (70). FIG. 6B shows the second device half (24) positioned proximate to an enterotomy (82) formed in the ileum (12). The enterotomy (90) is shown extending in a direction generally parallel the ileum (12), and it may be formed using any suitable cutting instrument (not shown) known in the art. The second suture device (36) is directed by a grasping instrument (92) to engage the tissue in which the enterotomy (90) is formed. Specifically, the first suture needle (64) is directed to pierce through a first lip (94) of the enterotomy (90), and the second suture needle (66) is directed to pierce through an opposed second lip (96) of the enterotomy (90).

The needles (64, 66) are then pulled by the grasping instrument (92) to thread respective end portions of the barbed suture (62) through the enterotomy lips (94, 96). Piercing and drawing of the needles (64, 66) through their respective lips (94, 96) may be performed in any order desired.

Piercing of the needles (64, 66) through the enterotomy lips (94, 96) as shown in FIG. 6A may be performed in successive steps using the grasping instrument (92), while the device half (24) is supported by a second grasping instrument (98) (see FIG. 6C). The grasping instruments (92, 98) may be of any suitable types known in the art. Additionally, after a needle (64, 66) is pierced and drawn through its respective lip (94, 96), the other needle (64, 66) may be positioned to magnetically couple with one of the magnetic members (54), thereby temporarily securing the inactive needle (64, 66) in place so the active needle (66) may be directed through its respective lip (94, 96), as shown in FIG. 6B.

FIG. 6C shows the second device half (24) being inserted through the enterotomy (90) using the second grasping instrument (98). Simultaneously, the suture needles (64, 66) and corresponding end portions of the barbed suture (62) are pulled away from the enterotomy (90) using the first grasping instrument (92). Because a medial portion of the suture (62) remains draped across and captures a medial portion of the rounded outer periphery (32) of the second device half (24), continued pulling of the barbed suture (62) via the suture needles (64, 66) draws the device half (24) closer against an inner surface of the ileum (12). Additionally, the barbs (68) of the barbed suture (62) (see FIG. 5B) anchor within the tissue to prevent unintentional loosening of the suture (62) relative to the enterotomy lips (94, 96).

As shown in FIG. 6D, the suture needles (64, 66) are then directed to suture the enterotomy (90) closed. For example, each suture needle (64, 66) and corresponding end portion of the suture (62) may be threaded through the first and second enterotomy lips (94, 96), back and forth in an alternating manner along a path extending from a first end of the enterotomy (90) to an opposed second end of the enterotomy (90). As described above, the barbed nature of the suture (62) prevents unintentional loosening of the suture (62), and thereby eliminates the need for tying knots to secure the suture (62) in place. In other variations, however, the suture (62) may be in the form of a non-barbed suture and may be secured by tying knots, applying clips, and/or otherwise secured according to various suitable methods known in the art. Following the step shown in FIG. 6D, excess end portions of the suture (62) are trimmed away and removed from the patient along with the suture needles (64, 66). As described above, the steps shown in FIGS. 6A-6D may be implemented for deploying the first device half (22) within the duodenum (8), before or after deploying the second device half (24) within the ileum (12).

FIG. 6E shows the first device half (22) sutured within the duodenum (8) and the second device half (24) sutured within an adjacent portion of the ileum (12), following completion of the steps shown in FIGS. 6A-6D for each of the device halves (22, 24). As indicated by the directional arrows in FIG. 6E, the adjacent portions of the duodenum (8) and the ileum (12) are then repositioned as necessary to arrange the first and second device halves (22, 24), anchored therein, in a confronting relationship in which the first mating surface (38) confronts the second mating surface (40).

As shown in FIG. 6F, once the device halves (22, 24) are brought within proximate range of each another, the magnetic members (54) of the device halves (22, 24) mutually attract one another and draw the two device halves (22, 24) together. As described in greater detail below, the device halves (22, 24) thereby compress the sidewalls of the duodenum (8) and the ileum (12) between their mating surfaces (38, 40), and cause the formation of an anastomosis.

FIG. 6G shows a cross-sectional view of the first and second device halves (22, 24), sutured within the duodenum (8) and ileum (12), respectively, in positions corresponding to those shown in FIG. 6F. The magnetic members (54) of the first device half (22) are within close enough range of the magnetic members (54) of the second device half (24) that the magnetic members (54) begin to attract one another through the tissue sidewalls (8, 12) and draw the two device halves (22, 24) together.

As shown in FIG. 6H, magnetic attraction between the magnetic members (54) operates to draw the device halves (22, 24) together and compress the sidewalls of the duodenum (8) and the ileum (12) between the first and second mating surfaces (38, 40). The contoured configuration of the mating surfaces (38, 40), described above, facilitates proper alignment of the device halves (22, 24) with one another as they draw together. Compression of the tissue sidewalls (8, 12) between the mating surfaces (38, 40) induces serosa-to-serosa adhesion between the sidewalls (8, 12) at a perimeter surrounding the device (20). Additionally, the compressive clamping force exerted by the mating surfaces (38, 40) is sufficient to cause ischemia and eventual necrosis in the clamped tissue. Advantageously, the smooth outer periphery and low-profile, pill-shaped configuration of the device (20) minimizes interference of fluid flow through the duodenum (8) and ileum (12) during the necrosis period.

With passage of time, such as approximately four days to two weeks, for example, the compressed tissue fully necroses between the device halves (22, 24) and detaches from the surrounding healthy tissue (8, 12), now bonded together via serosa-to-serosa adhesion. As shown in FIG. 6G, detachment of the necrosed tissue from the surrounding healthy tissue (8, 12) releases the tissue compression device (20) into the small intestine (5), and reveals a formed anastomosis (18). The device (20) continues on through the large intestine (6) and is eventually passed by the patient. The smooth outer periphery and low-profile, pill-shaped configuration of the device (20) facilitates downstream passage of the device (20) through the gastrointestinal tract (2), including the ileocecal valve (17), for example.

C. Exemplary Alternative Anastomosis Tissue Compression Device Having Lug Members In some suturing procedures employed for anchoring halves of a tissue compression device within adjacent anatomical structures for forming an anastomosis therebetween, it may be desirable to couple the first device half with the second device half using sutures. An alternative tissue compression device having exemplary features that enable this technique is described in greater detail below.

Figure 7:
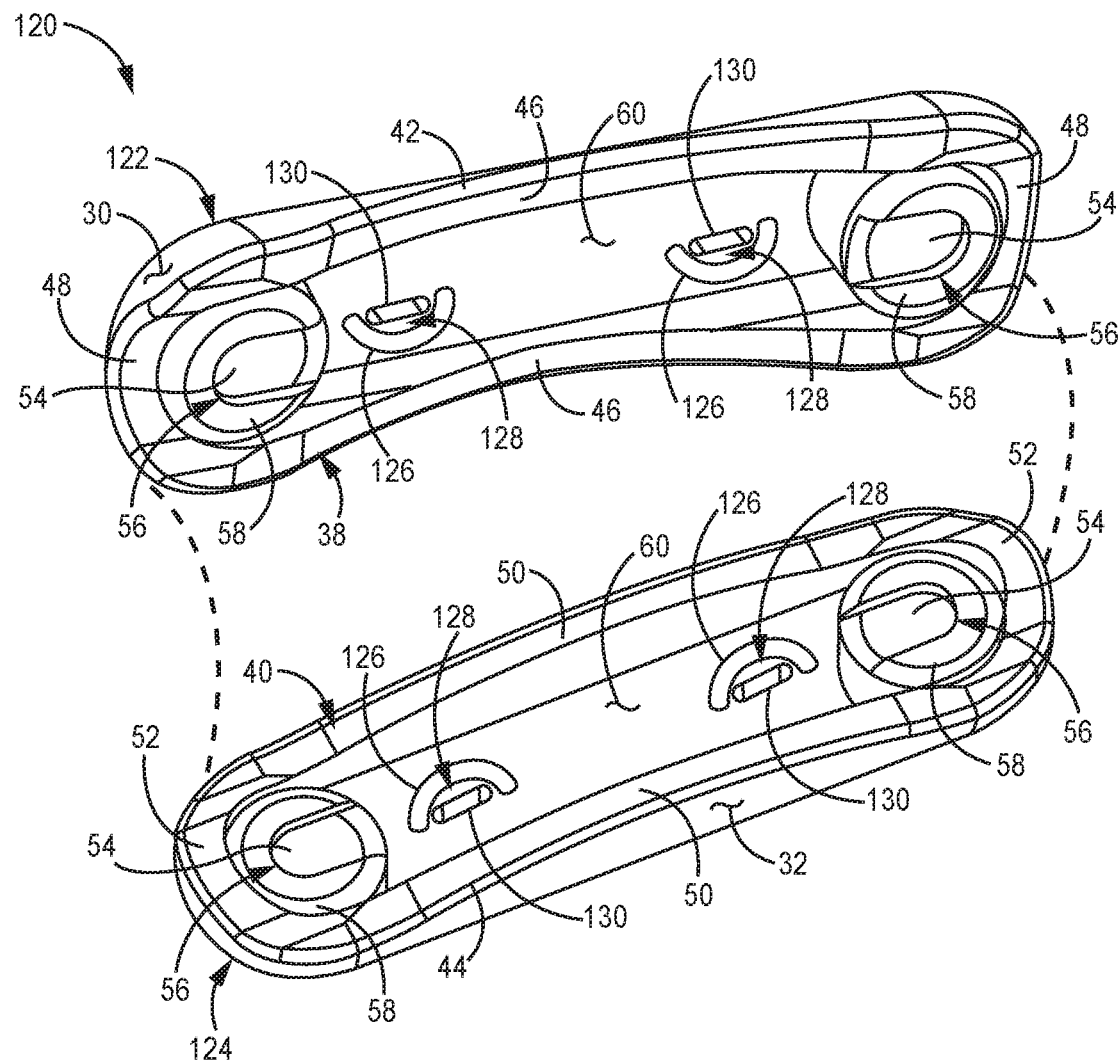
FIG. 7 depicts a disassembled perspective view of another exemplary tissue compression device for forming an anastomosis.

FIG. 7 shows an exemplary alternative tissue compression device (120) for forming an anastomosis, such as a side-by-side anastomosis. The device (120) includes a first device half (122) and a second device half (124) that are similar in structure to the first and second device halves (22, 24), respectively, of tissue compression device (20) described above, as indicated by the use of like reference numerals in FIG. 7. Features labeled with like reference numerals in FIG. 7 will not be described in detail below, and it will be understood that these features embody the structural and functional characteristics of the corresponding features as described above in connection with tissue compression device (20). Unique features of the tissue compression device (120) are described in greater detail below.

In place of the suture needle clip members (70) and suture posts (76) of tissue compression device (20), each device half (122, 124) in the present example includes a pair of lug members (126) coupled to and projecting from the respective recessed base wall (60). As described below, each lug member (126) functions as an alternative type of suture retaining structure configured to retain a suture. Each lug member (126) is arranged proximate to a respective one of the magnet retaining structures (58), and is oriented so as to extend generally along a longitudinal centerline of the respective base wall (60), parallel to a length of the respective device half (22, 24). Each lug member (126) is shown in the form of an arcuate structure having rounded ends and an opening (128) extending laterally between the rounded ends. The opening (128) is sized to slidably receive a suture device therethrough, including a suture and corresponding suture needles, as described in greater detail below in connection with FIGS. 8A-8G. In alternative variations, the lug members (126) may be formed with various other shapes having an opening suitably sized to receive a suture device therethrough.

Each device half (122, 124) also includes a pair of suture bores (130). Each suture bore (130) is aligned with a respective lug member (126) and extends through the recessed base wall (60), transversely away from the device axis, and opens to the rounded outer periphery (30, 32) of the respective device half (122, 124). Similar to suture bores (74) of device (20), suture bores (130) are sized to slidably receive a suture device therethrough, including a suture and corresponding suture needles, as described in greater detail below in connection with FIGS. 8A-8G. While each suture bore (130) of the present example is shown formed with an elongate profile shape, in other examples each suture bore (130) may be formed with a generally circular profile shape similar to suture bores (74) of device (20), for example.

Each device half (122, 124) of tissue compression device (120) may be equipped with a respective suture device, similar to suture devices (34, 36) described above in connection with device (20) shown in FIG. 5A. Further, the device halves (122, 124) such suture devices may be packaged together in the form of an anastomosis tissue compression device kit. In this manner, the tissue compression device (120) may be delivered to a medical professional as a convenient assembly containing necessary suture materials for deploying the device (120) within a patient. In that regard, though not shown, each device half (122, 124) may further include one or more additional suture device retaining structures similar to needle clip members (70) and/or suture posts (76) of tissue compression device (20), described above, for example.

D. Exemplary Method of Anchoring Tissue Compression Device Having Lug Members

Having described structural features of the tissue compression device (120) above, an exemplary method of anchoring the first and second device halves (22, 24) within respective portions of a patient's gastrointestinal tract (2) is described below in connection with FIGS. 8A-8G. While the first and second device halves (122, 124) are shown and described as being deployed within the duodenum (8) and the ileum (12), respectively, it will be understood that the device halves (122, 124) may be deployed at various other locations within the gastrointestinal tract (2), or within other organs, at which an anastomosis is to be formed.

Figure 8A:
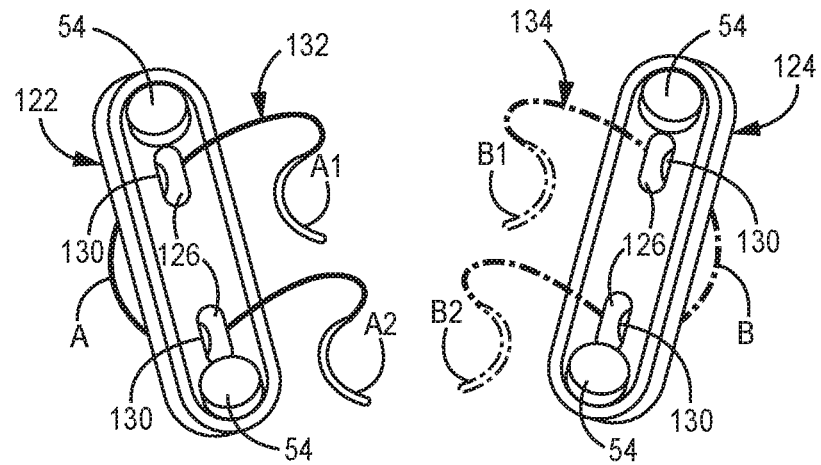
FIG. 8A depicts a perspective view of first and second device halves of the tissue compression device of FIG. 7, equipped with first and second suture devices, respectively, arranged according to an initial step of another exemplary suturing procedure.

FIG. 8A shows an initial step of the exemplary anchoring procedure in which the first and second device halves (22, 24) are separated from one another. The first device half (122) is arranged with a first suture device (132), and the second device half (124) is arranged with a second suture device (134). The first suture device (132) includes a first suture (A) and first and second suture needles (A1, A2) coupled to opposed ends of the first suture (A). The second suture device (134) includes a second suture (B) and first and second suture needles (B1, B2) coupled to opposed ends of the second suture (B). The sutures (A, B) are shown in the form of barbed sutures, similar to barbed sutures (62) described above, and the suture needles (A1, A2, B1, B2) are shown in the form of curved suture needles. In alternative versions, the sutures (A, B) may be non-barbed sutures.

In the initial step shown in FIG. 8A, the first suture device (132) is threaded through the suture bores (130) of the first device half (122), and the second suture device (134) is threaded through the suture bores (130) of the second device half (124). Specifically, the first suture needle (A1) and a corresponding first end portion of the first suture (A) is directed through a first suture bore (130) of the first device half (122) in a direction toward the device axis. Similarly, the second suture needle (A2) and a corresponding second end portion of the first suture (A) is directed through a second suture bore (130) of the first device half (122), in a direction toward the device axis. This arrangement leaves a medial portion of the first suture (A) draped across and capturing a medial portion of the rounded outer periphery (30) of the first device half (122), located between the suture bores (130). The second suture device (134) is arranged relative to the second device half (124) in a similar manner. The device halves (122, 124) are then arranged relative to one another so that their mating surfaces (38, 40) face generally toward each other.

Figure 8B:
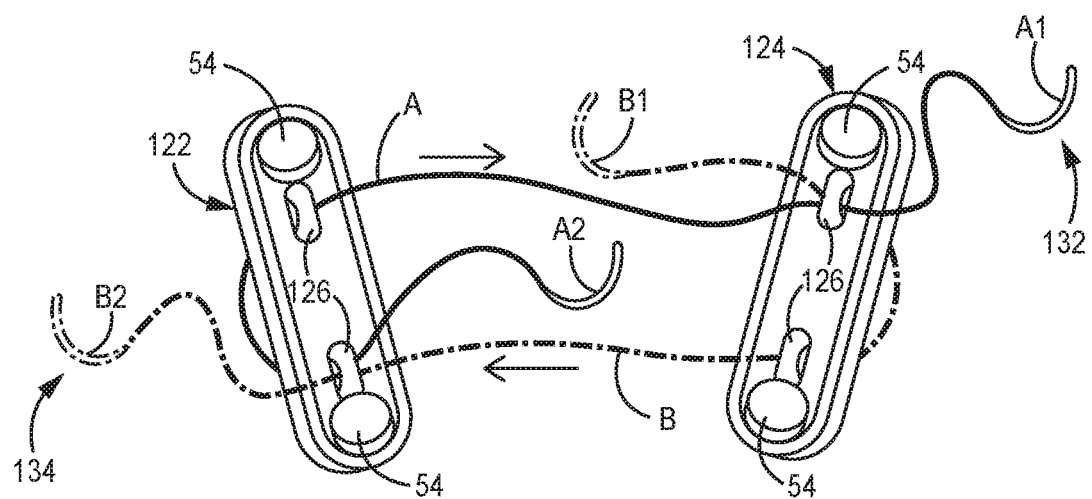
FIG. 8B depicts a perspective view of the first and second device halves of FIG. 7, showing the first and second suture devices arranged according to another step of the exemplary suturing procedure of FIG. 8A.

As shown in FIG. 8B, the first suture needle (A1) and corresponding first end portion of the first suture (A) are threaded through a first lug member (126) of the second device half (124). Additionally, the second suture needle (B2) and corresponding second end portion of the second suture (B) are threaded through a second lug member (126) of the first device half (122). As shown, the lug members (126) through which the needles (A1, B2) are threaded are arranged at opposite ends of the respective device halves (122, 124).

To prevent tangling of the sutures (A, B) during this step, any needle (A1, A2, B1, B2) not actively being manipulated may be magnetically coupled to one of the magnetic members (54) of a proximately located device half (122, 124). In that regard, each suture needle (A1, A2, B1, B2) may comprise a ferrous material. By way of example only, after the first needle (A1) is threaded through the first lug member (126) of the second device half (124), the needle (A1) may be positioned to contact or otherwise magnetically couple with the adjacent magnetic member (54) of the second device half (124). Further, it will be understood that the step shown in FIG. 8B may be performed extracorporeally, prior to deploying the device halves (122, 124) within the patient. In alternative variations of the procedure, one or both portions of the step shown in FIG. 8B may be performed intracorporeally, after the device halves (122, 124) have been deployed within the patient.

Figure 8C:
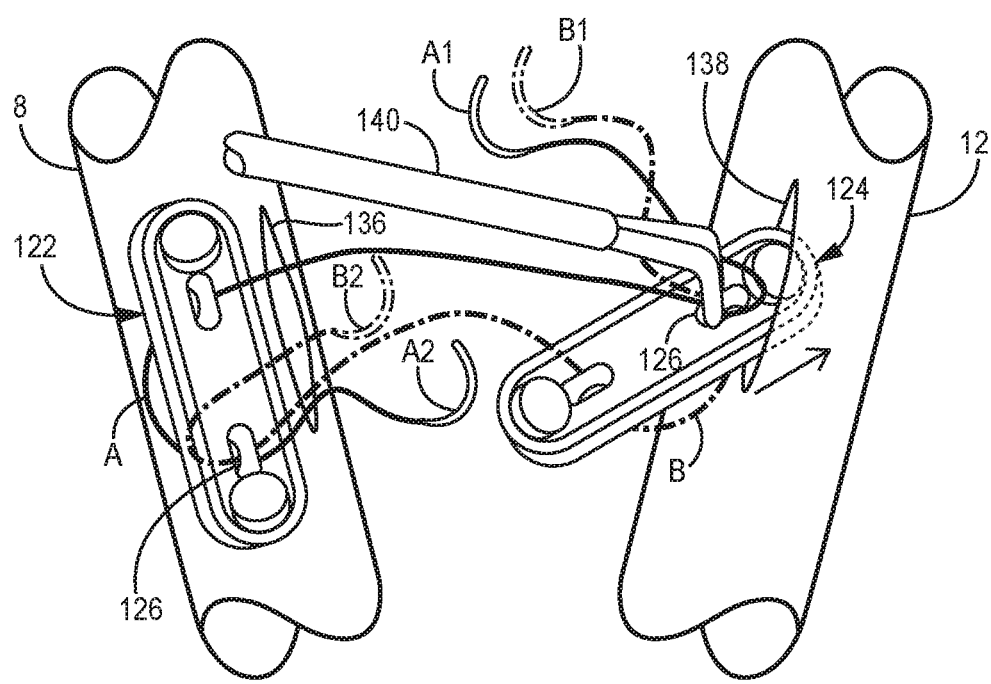
FIG. 8C depicts a perspective of the first and second device halves of FIG. 7, showing the first device half arranged within a first portion of a small intestine and the second device half being inserted into a second portion of the small intestine according to another step of the exemplary suturing procedure of FIG. 8A.

FIG. 8C shows the first device half (122) after having been deployed within the patient's duodenum (8) through a first enterotomy (136), and the second device half (124) being actively inserted into an adjacent portion of the patient's ileum (12) through a second enterotomy (138), using a grasping instrument (140). The grasping instrument (140) may be of any suitable type known in the art. Each enterotomy (136, 138) is shown extending in a direction generally parallel to the portion of the duodenum (8) or ileum (12) in which it is formed. The enterotomies (136, 138) may be formed using any suitable cutting instrument (not shown) known in the art. As described above, the deployment step shown in FIG. 8C may be performed after or before the inter-threading step shown in FIG. 8B. In the present example in which the deployment step of FIG. 8C is performed after the inter-threading step of FIG. 8B, the suture needles (A1, A2, B1, B2) are maintained externally of the duodenum (8) and the ileum (12) while the device halves (122, 124) are inserted through the enterotomies (136, 138).

Figure 8D:
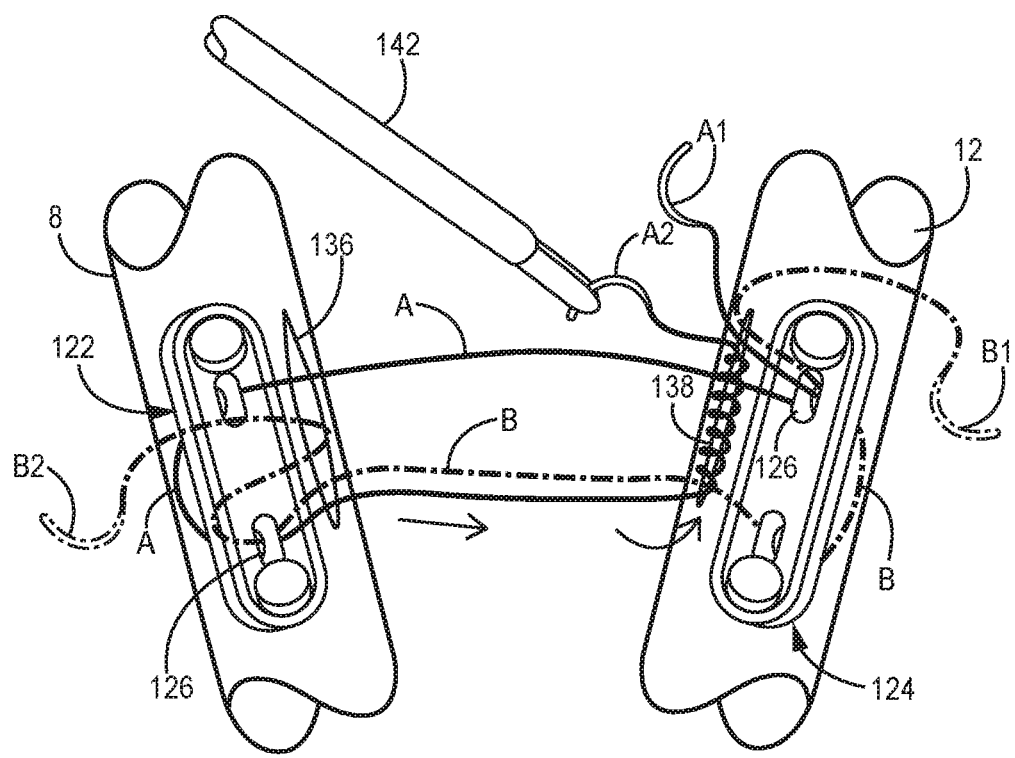
FIG. 8D depicts a perspective view of the first and second device halves of FIG. 7, showing the first device half arranged within the first portion of the small intestine and the second device half arranged within the second portion of the small intestine portion, and the first and second suture devices arranged according to another step of the exemplary suturing procedure of FIG. 8A.
Figure 8E:
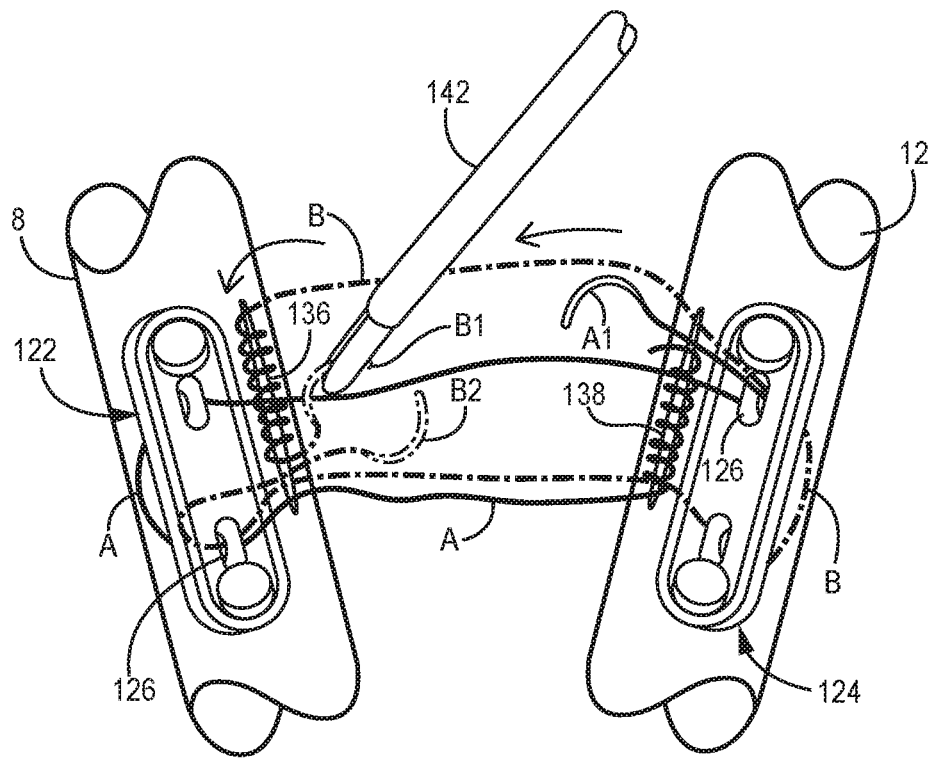
FIG. 8E depicts a perspective view of the first and second device halves of FIG. 7 arranged within the first and second small intestine portions, showing the first and second suture devices arranged according to another step of the exemplary suturing procedure of FIG. 8A.

As shown in FIGS. 8D and 8E, once the device halves (122, 124) have been deployed within the duodenum (8) and the ileum (12), respectively, the second enterotomy (138) in the ileum (12) is sutured closed with the first suture device (132), and the first enterotomy (136) in the duodenum (8) is sutured closed with the second suture device (134). Another exemplary grasping instrument (142) is used to facilitate this step. More specifically, as shown in FIG. 8D, the second suture needle (A2) and corresponding second end portion of the first suture (A) are threaded by the grasping instrument (142) through the lips of the second enterotomy (138), back and forth in an alternating manner along a path extending from a first end of the enterotomy (138) to an opposed second end of the enterotomy (138). The second needle (A2) is then removed from the first suture (A).

As shown in FIG. 8E, the first suture needle (B1) and corresponding first end portion of the second suture (B) are threaded by the grasping instrument (142) through the lips of the first enterotomy (136), back and forth in an alternating manner along a path extending from a first end of the enterotomy (136) to an opposed second end of the enterotomy (136). The first needle (B1) is then removed from the second suture (B). It will be understood that the step shown in FIG. 8E may be performed immediately after or immediately before the step shown in FIG. 8D.

Figure 8G:
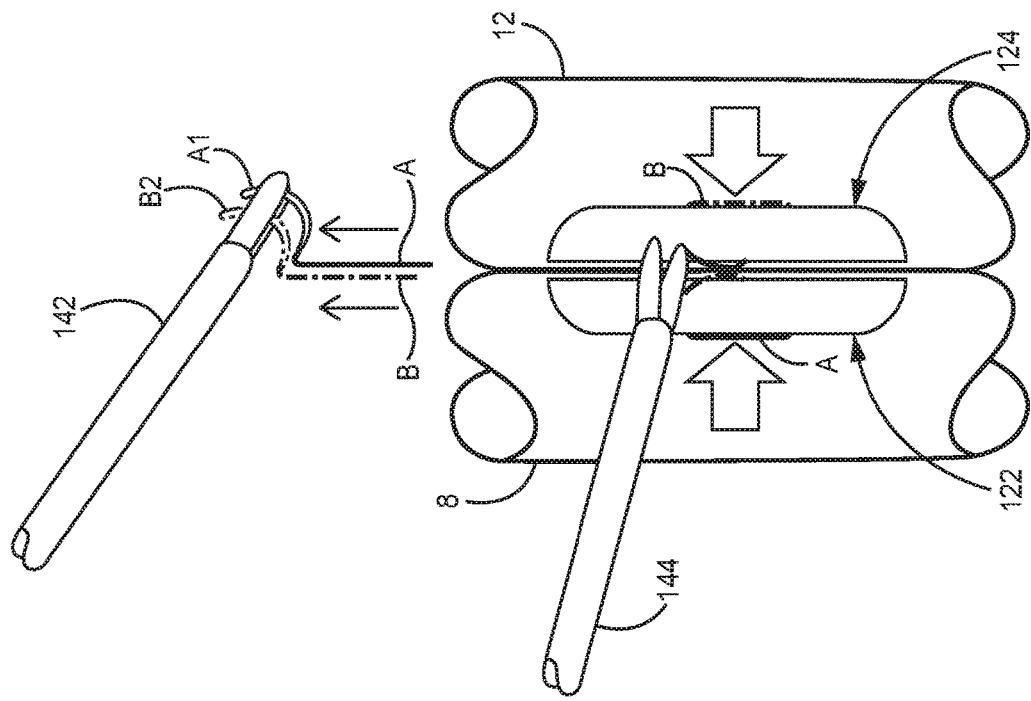
FIG. 8G depicts a perspective view of the first and second device halves of FIG. 7 arranged within the first and second small intestine portions, showing the first and second suture devices arranged according to another step of the exemplary suturing procedure of FIG. 8A in which ends of the suture devices have been pulled tight to bring the first and second device halves into confronting relation.
Figure 8F:
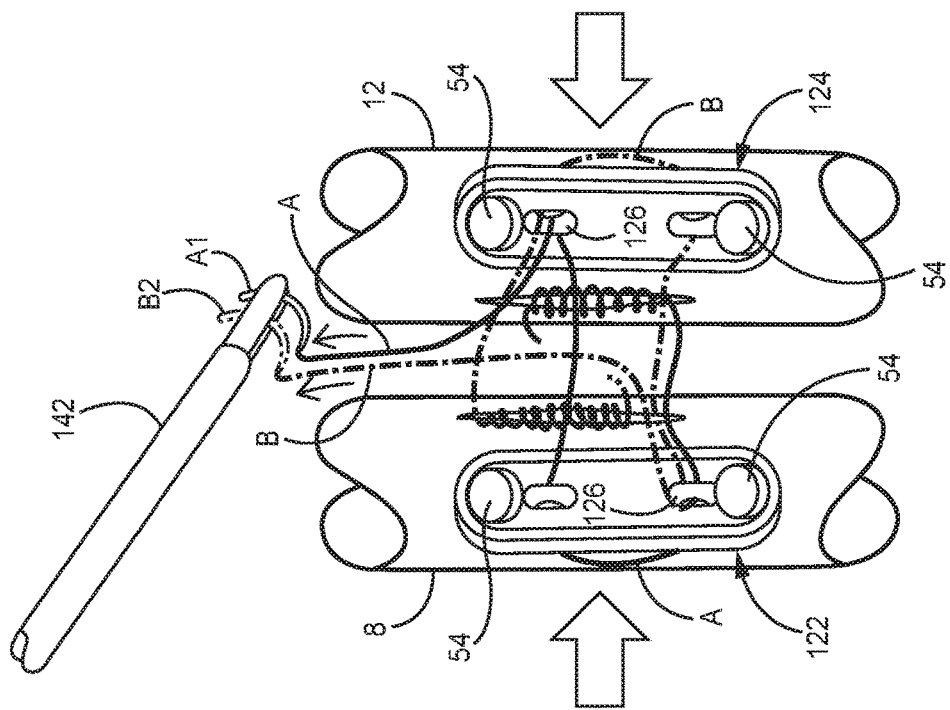
FIG. 8F depicts a perspective view of the first and second device halves of FIG. 7 arranged within the first and second small intestine portions, showing the first and second suture devices arranged according to another step of the exemplary suturing procedure of FIG. 8A.

As shown in FIG. 8F, as a result of completing the steps shown in FIGS. 8A-8E, the second end portion of the first suture (A) is anchored to the ileum (12), and a medial portion of the first suture (A) is looped through the suture bores (130) of the first device half (122) and through a first lug member (126) of the second device half (124). Additionally, the first end portion of the second suture (B) is anchored to the duodenum (8), and a medial portion of the second suture (B) is looped through the suture bores (130) of the second device half (124) and through a second lug member (126) of the first device half (122). Accordingly, the first and second device halves (122, 124) are coupled with one another via the first and second sutures (A, B).

The resulting suture configuration shown in FIG. 8F enables the remaining suture needles (A1, B2) to be pulled in a direction away from the device halves (122, 124) to tighten the sutures (A, B) and thereby draw the device halves (122, 124) toward one another into a confronting arrangement. In particular, pulling the first suture (A) via remaining needle (A1) draws the second device half (124), via its captured lug member (126), in a direction toward the duodenum (8) and against an inner surface of the ileum (12). Pulling the first suture (A) simultaneously draws the first device half (122), via a captured medial portion of its outer periphery (30), in a direction toward the ileum (12) and against an inner surface of the duodenum (8). Additionally, pulling the second suture (B) via remaining needle (B2) draws the first device half (122), via its captured lug member (126), in a direction toward the ileum (12) and against the inner surface of the duodenum (8). Pulling the second suture (B) simultaneously draws the second device half (124), via a captured medial portion of its outer periphery (32), in a direction toward the duodenum (8) and against the inner surface of the ileum (12).

As the sutures (A, B) are pulled tighter, the duodenum (8) and ileum (12) are drawn together, and the device halves (122, 124) are brought within close enough range of each other that their magnetic members (54) mutually attract and couple the device halves (122, 124) together in magnetic engagement, as shown in FIG. 8G. As described above, the sutures (A, B) are shown in the form of barbed sutures having outwardly projecting barbs (see FIG. 5B) configured to penetrate and anchor within tissue. The barbed nature of the sutures (A, B) prevents unintentional loosening of the sutures (A, B) within the duodenum (8) and ileum (12), and thus eliminates the need for tying knots to secure the sutures (A, B) in place. Accordingly, once the sutures (A, B) have been drawn tight, the free ends of the of the sutures (A, B) may be simply trimmed way with a cutting instrument (144) to complete the suturing procedure. In other variations, the sutures (A, B) may be in the form of non-barbed sutures, and may be secured by tying knots, applying clips, or otherwise securing the sutures according to various methods known in the art.

Following completion of the exemplary suturing procedure shown in FIGS. 8A-8G, the device halves (122, 124) continue to exert a magnetically-induced compressive force on the tissue positioned between their mating surfaces (38, 40). As described above in connection with FIGS. 6G-6I, passage of time yields tissue ischemia and eventual necrosis. Ultimately, the clamped tissue fully necroses and the compression device (20) falls away to reveal an anastomosis (18) between the duodenum (8) and the ileum (12). The detached device (120) is then released into the small intestine (5) and continues downstream through the large intestine (6), and is eventually passed by the patient.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A tissue compression device for forming an anastomosis between first and second anatomical structures, the device comprising: (a) a first device portion including: (i) a first mating surface, (ii) a first base wall recessed from the first mating surface so as to define a first inner recess within the first device portion, and (iii) a first set of suture bores extending through the first base wall and opening to an outer periphery of the first device portion; and (b) a second device portion including: (i) a second mating surface, (ii) a second base wall recessed from the second mating surface so as to define a second inner recess within the second device portion, and (iii) a second set of suture bores extending through the second base wall and opening to an outer periphery of the second device portion, wherein the first and second device portions are configured to compress tissue positioned between the first and second mating surfaces.

Example 2

The tissue compression device of Example 1, wherein the first device portion further includes at least one first needle retaining structure configured to releasably engage and support at least one first suture needle within the first inner recess, wherein the second device portion further includes at least one second needle retaining structure configured to releasably engage and support at least one second suture needle within the second inner recess.

Example 3

The tissue compression device of Example 2, wherein the at least one first needle retaining structure is coupled to the first base wall, and the at least one second needle retaining structure is coupled to the second base wall.

Example 4

The tissue compression device of Example 3, wherein the at least one first needle retaining structure includes a first pair of needle retaining structures configured to releasably engage and support a first pair of suture needles, wherein the at least one second needle retaining structure includes a second pair of needle retaining structures configured to releasably engage and support a second pair of suture needles.

Example 5

The tissue compression device of any one or more of Examples 2 through 4, wherein each of the needle retaining structures includes a clip member having a pair of clip arms configured to releasably engage a respective suture needle.

Example 6

The tissue compression device of any one or more of Examples 1 through 5, wherein the first device portion further includes a first suture retaining structure configured to retain at least a portion of a first suture within the first inner recess, wherein the second device portion further includes a second suture retaining structure configured to retain at least a portion of a second suture within the second inner recess.

Example 7

The tissue compression device of Example 6, wherein the first suture retaining structure projects from the first base wall, and the second suture retaining structure projects from the second base wall.

Example 8

The tissue compression device of any one or more of Examples 1 through 7, further comprising the first device portion further includes at least one first lug member, and the second device portion further includes at least one second lug member, wherein each of the lug members is configured to receive a suture therethrough for anchoring the respective device portion relative to an anatomical structure.

Example 9

The tissue compression device of Example 8, wherein the at least one first lug member is coupled to the first base wall, and the at least one second lug member is coupled to the second base wall.

Example 10

The tissue compression device of any one or more of Examples 1 through 9, further comprising a first magnetic member supported by the first device portion, and a second magnetic member supported by the second device portion, wherein the magnetic members are configured to magnetically attract one another and thereby draw the first and second device portions together to compress tissue positioned between the first and second mating surfaces Example 11

The tissue compression device of any one or more of Examples 1 through 10, wherein the first mating surface includes a first contoured portion shaped with a first contour, and the second mating surface includes a second contoured portion shaped with a second contour that complements the first contour, wherein the contoured portions are configured to mate with one another to facilitate alignment of the first device portion with the second device portion.

Example 12

The tissue compression device of any one or more of Example 1 through 11, wherein each of the first and second device portions includes a body having a unitary structure formed with a length greater than its width.

Example 13

An anastomosis tissue compression device kit, comprising: (a) the tissue compression device of any one or more of Examples 1 through 12; (b) a first suture device including a first suture and a first pair of suture needles coupled to opposed ends of the first suture; and (c) a second suture device including a second suture and a second pair of suture needles coupled to opposed ends of the second suture, wherein at least a portion of the first suture device is retained within the first inner recess of the first device portion, wherein at least a portion of the second suture device is retained within the second inner recess of the second device portion.

Example 14

The anastomosis tissue compression device kit of Example 13, wherein at least one of the first or second device portions further includes at least one of: (a) a suture needle retaining structure configured to releasably engage and support at least one of the suture needles; (b) a suture retaining structure configured to retain at least one of the sutures; or (c) a lug member configured to receive a suture therethrough.

Example 15

The anastomosis tissue compression device kit of any one or more of Examples 13 through 14, wherein at least one of the first or second sutures includes a barbed suture.

Example 16

The anastomosis tissue compression device kit of any one or more of Examples 13 through 15, wherein at least one of the suture needles includes a curved suture needle.

Example 17

A tissue compression device for forming an anastomosis between first and second anatomical structures, the device comprising: (a) a first device portion including: (i) a first mating surface, (ii) a first base wall recessed from the first mating surface so as to define a first inner recess within the first device portion, and (iii) a first retaining structure arranged within the first inner recess and being configured to engage and retain at least a portion of a first suture device; and (b) a second device portion including: (i) a second mating surface, (ii) a second base wall recessed from the second mating surface so as to define a second inner recess within the second device portion, and (iii) a second retaining structure arranged within the second inner recess and being configured to engage and retain at least a portion of a second suture device; and wherein the first and second device portions are configured to magnetically attract one another to compress tissue positioned between the first and second mating surfaces.

Example 18

The tissue compression device of Example 17, wherein each of the first and second device portions further includes at least two suture bores extending through the device portion.

Example 19

A method of anchoring a tissue compression device within first and second anatomical structures for forming an anastomosis therebetween, the tissue compression device including first and second device halves, the method comprising: (a) arranging a first barbed suture relative to the first device half such that: (i) a first end of the first barbed suture extends through a first suture bore formed in the first device half, (ii) a second end of the first barbed suture extends through a second suture bore formed in the first device half, and (iii) a medial portion of the first barbed suture extends between the first and second suture bores and across an outer periphery of the first device half; (b) arranging a second barbed suture relative to the second device half such that: (i) a first end of the second barbed suture extends through a third suture bore formed in the second device half, (ii) a second end of the second barbed suture extends through a fourth suture bore formed in the second device half, and (iii) a medial portion of the second barbed suture extends between the third and fourth suture bores and across an outer periphery of the second device half; (c) after steps (a) and (b), threading the first end of the first barbed suture through a portion of the second device half, and threading the second end of the second barbed suture through a portion of the second device half; (d) after steps (a) and (b), inserting the first device half through a first enterotomy formed in a sidewall of the first anatomical structure, and inserting the second device half through a second enterotomy formed in a sidewall of the second anatomical structure; (e) after steps (a)-(d), suturing the second enterotomy at least partially closed with the second end of the first barbed suture, and suturing the first enterotomy at least partially closed with the first end of the second barbed suture; and (f) after step (e), pulling each of the first end of the first barbed suture and the second end of the second barbed suture in a direction away from the at least partially closed enterotomies to thereby draw the first and second device halves toward one another with the sidewalls of the anatomical structures positioned therebetween.

Example 20

The method of Example 19, wherein the first device half includes a first magnetic member and the second device half includes a second magnetic member configured to magnetically attract the first magnetic member, and wherein step (f) includes pulling the first end of the first barbed suture and the second end of the second barbed suture to bring the first and second magnetic members within a proximity of one another that enables the magnetic members to magnetically draw the first and second device halves together and compress the sidewalls of the anatomical structures between the device halves.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the devices may be disassembled, and any number of the particular pieces or parts of the devices may be selectively replaced or removed in any combination. Upon cleaning and/or replacement of particular parts, some versions of the devices may be reassembled for subsequent use either at a reconditioning facility, or by a user immediately prior to a procedure. Those skilled in the art will appreciate that reconditioning of a devices may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A tissue compression device for forming an anastomosis between first and second anatomical structures, the device comprising:
   (a) a first device portion including:
      (i) a first mating surface,
      (ii) a first base wall recessed from the first mating surface so as to define a first inner recess within the first device portion, and
      (iii) a first set of suture bores extending through the first base wall and opening to an outer periphery of the first device portion;
   (b) a second device portion including:
      (i) a second mating surface,
      (ii) a second base wall recessed from the second mating surface so as to define a second inner recess within the second device portion, and
      (iii) a second set of suture bores extending through the second base wall and opening to an outer periphery of the second device portion; and
   (c) a needle retaining structure configured to releasably engage and support a suture needle within at least one of the first inner recess or the second inner recess,
   wherein the first and second device portions are configured to compress tissue positioned between the first and second mating surfaces.

2. The tissue compression device of claim 1, wherein the needle retaining structure comprises at least one first needle retaining structure configured to releasably engage and support at least one first suture needle within the first inner recess,
   wherein the second device portion further includes at least one second needle retaining structure configured to releasably engage and support at least one second suture needle within the second inner recess.

3. The tissue compression device of claim 2, wherein the at least one first needle retaining structure is coupled to the first base wall, and the at least one second needle retaining structure is coupled to the second base wall.

4. The tissue compression device of claim 3, wherein the at least one first needle retaining structure includes a first pair of needle retaining structures configured to releasably engage and support a first pair of suture needles,
   wherein the at least one second needle retaining structure includes a second pair of needle retaining structures configured to releasably engage and support a second pair of suture needles.

5. The tissue compression device of claim 2, wherein each of the needle retaining structures includes a clip member having a pair of clip arms configured to releasably engage a respective suture needle.

6. The tissue compression device of claim 1, wherein the first device portion further includes a first suture retaining structure configured to retain at least a portion of a first suture within the first inner recess,
   wherein the second device portion further includes a second suture retaining structure configured to retain at least a portion of a second suture within the second inner recess.

7. The tissue compression device of claim 6, wherein the first suture retaining structure projects from the first base wall, and the second suture retaining structure projects from the second base wall.

8. The tissue compression device of claim 1, wherein the first device portion further includes at least one first lug member, and the second device portion further includes at least one second lug member,
   wherein each of the lug members is configured to receive a suture therethrough for anchoring the respective device portion relative to an anatomical structure.

9. The tissue compression device of claim 8, wherein the at least one first lug member is coupled to the first base wall, and the at least one second lug member is coupled to the second base wall.

10. The tissue compression device of claim 1, further comprising a first magnetic member supported by the first device portion, and a second magnetic member supported by the second device portion,
    wherein the magnetic members are configured to magnetically attract one another and thereby draw the first and second device portions together to compress tissue positioned between the first and second mating surfaces.

11. The tissue compression device of claim 1, wherein the first mating surface includes a first contoured portion shaped with a first contour, and the second mating surface includes a second contoured portion shaped with a second contour that complements the first contour,
    wherein the contoured portions are configured to mate with one another to facilitate alignment of the first device portion with the second device portion.

12. The tissue compression device of claim 1, wherein each of the first and second device portions includes a body having a unitary structure formed with a length greater than its width.

13. An anastomosis tissue compression device kit, comprising:
(a) the tissue compression device of claim 1;
(b) a first suture device including a first suture and a first pair of suture needles coupled to opposed ends of the first suture; and
(c) a second suture device including a second suture and a second pair of suture needles coupled to opposed ends of the second suture,
wherein at least a portion of the first suture device is retained within the first inner recess of the first device portion,
wherein at least a portion of the second suture device is retained within the second inner recess of the second device portion.

14. The anastomosis tissue compression device kit of claim 13, wherein at least one of the first or second device portions further includes at least one of:
(a) a suture retaining structure configured to retain at least one of the first suture or the second suture; or
(b) a lug member configured to receive at least one of the first suture or the second suture therethrough.

15. The anastomosis tissue compression device kit of claim 13, wherein at least one of the first or second sutures includes a barbed suture.

16. The anastomosis tissue compression device kit of claim 13, wherein at least one of the suture needles includes a curved suture needle.

17. A tissue compression device for forming an anastomosis between first and second anatomical structures, the device comprising:
(a) a first device portion including:
(i) a first mating surface,
(ii) a first base wall recessed from the first mating surface so as to define a first inner recess within the first device portion, and
(iii) a first retaining structure arranged within the first inner recess and being configured to engage and retain at least a portion of a first suture device; and
(b) a second device portion including:
(i) a second mating surface,
(ii) a second base wall recessed from the second mating surface so as to define a second inner recess within the second device portion, and
(iii) a second retaining structure arranged within the second inner recess and being configured to engage and retain at least a portion of a second suture device; and
wherein the first and second device portions are configured to magnetically attract one another such that the first and second base walls face toward one another to compress tissue positioned between the first and second mating surfaces.

18. The tissue compression device of claim 17, wherein each of the first and second device portions further includes at least two suture bores extending through the device portion.

19. A tissue compression device for forming an anastomosis between first and second anatomical structures, the device comprising:
(a) a first device portion including:
(i) a first mating surface, and
(ii) a first clip member configured to releasably retain a portion of a first suture device; and
(b) a second device portion including:
(i) a second mating surface, and
(ii) a second clip member configured to releasably retain a portion of a second suture device,
wherein the first and second device portions are configured to magnetically attract one another and thereby compress tissue positioned between the first and second mating surfaces.

20. The tissue compression device of claim 19, wherein the first clip member is disposed between first and second side portions of the first mating surface, wherein the second clip member is disposed between first and second side portions of the second mating surface.

* * * * *